(12) United States Patent
Kim et al.

(10) Patent No.: US 11,759,570 B2
(45) Date of Patent: Sep. 19, 2023

(54) MEDICAMENT INJECTOR AND INTERCHANGEABLE CARTRIDGES THEREFOR

(71) Applicant: Difinity Solutions Inc., Nanaimo (CA)

(72) Inventors: David Sanghyuck Kim, Nanaimo (CA); Damien Tak, Nanaimo (CA)

(73) Assignee: Difinity Solutions Inc., Vancouver (CA)

( * ) Notice: Subject to any disclaimer, the term of this patent is extended or adjusted under 35 U.S.C. 154(b) by 625 days.

(21) Appl. No.: 16/800,804

(22) Filed: Feb. 25, 2020

(65) Prior Publication Data
US 2020/0268971 A1 Aug. 27, 2020

Related U.S. Application Data

(60) Provisional application No. 62/810,121, filed on Feb. 25, 2019.

(51) Int. Cl.
*A61M 5/20* (2006.01)
*A61M 5/24* (2006.01)
*A61M 11/00* (2006.01)

(52) U.S. Cl.
CPC ........ *A61M 5/2033* (2013.01); *A61M 5/2459* (2013.01); *A61M 11/007* (2014.02); *A61M 2005/2433* (2013.01); *A61M 2205/12* (2013.01)

(58) Field of Classification Search
CPC .... A61M 5/19; A61M 5/2046; A61M 5/2033; A61M 2005/1787; A61M 5/2459; A61M 11/007; A61M 2005/2433; A61M 2205/12
See application file for complete search history.

(56) References Cited

U.S. PATENT DOCUMENTS

| | | | |
|---|---|---|---|
| 1,557,836 A | 10/1925 | Hein | |
| 2,922,419 A | 1/1960 | Bednarz | |

(Continued)

FOREIGN PATENT DOCUMENTS

| | | |
|---|---|---|
| CA | 2049972 | 5/2000 |
| EP | 3122400 | 7/2019 |

(Continued)

OTHER PUBLICATIONS

International Search Report issued on PCT/CA2020/051157 dated Oct. 15, 2020.

(Continued)

*Primary Examiner* — Amber R Stiles
*Assistant Examiner* — Nelson Louis Alvarado, Jr.
(74) *Attorney, Agent, or Firm* — Oyen Wiggs Green & Mutala LLP; Nicholas Garner

(57) ABSTRACT

The present invention relates to a medicament injector including an applicator with a cartridge-accepting receptacle. The medicament injector includes interchangeable, pre-filled medicament-containing cartridges. Each cartridge includes at least one barrier member having a closed position in which access to the medicament is inhibited. The barrier member is moveable from the closed position to an open position, in which the medicament is accessible via the applicator, when the cartridge is inserted into the cartridge-accepting receptacle. The barrier member moves back to the closed position when the cartridge is removed from the cartridge-accepting receptacle. This allows for a plurality of pre-filled medicament cartridges to be selected on demand via a need-based scenario for quick assembly with the medicament injector for use in various clinical scenarios to reduce the bulk, errors, complexity, and steps in medicament delivery while increasing the versatility, safety, and speed of medicament delivery in time critical situations.

30 Claims, 26 Drawing Sheets

(56) References Cited

U.S. PATENT DOCUMENTS

| | | |
|---|---|---|
| 3,134,380 A | 5/1964 | Armao |
| 3,378,008 A | 4/1968 | Ogle |
| 3,580,251 A | 5/1971 | Bourron-Marlotte |
| 3,659,587 A | 5/1972 | Baldwin |
| 3,659,602 A | 5/1972 | Cloyd |
| 3,850,174 A | 11/1974 | Ayres |
| 4,725,267 A | 2/1988 | Vaillancourt |
| 4,735,618 A | 4/1988 | Hagen |
| 4,747,829 A | 5/1988 | Jacob et al. |
| 4,767,413 A | 8/1988 | Haber et al. |
| 4,929,237 A | 5/1990 | Medway |
| 5,114,404 A | 5/1992 | Paxton et al. |
| 5,135,510 A | 8/1992 | Maszkiewicz et al. |
| 5,147,323 A | 9/1992 | Haber |
| 5,195,983 A | 3/1993 | Boese |
| 5,222,945 A | 6/1993 | Basnight |
| 5,269,761 A | 12/1993 | Stehrenberger et al. |
| 5,279,586 A | 1/1994 | Balkwill |
| 5,354,284 A | 10/1994 | Haber et al. |
| 5,425,715 A | 6/1995 | Dalling et al. |
| 5,472,430 A | 12/1995 | Vaillancourt et al. |
| 5,637,094 A | 6/1997 | Stewart, Jr. |
| 5,695,472 A | 12/1997 | Wyrick |
| 5,893,845 A | 4/1999 | Newby et al. |
| 5,980,494 A | 11/1999 | Malencheck et al. |
| 6,416,497 B1 | 7/2002 | Kirk |
| 6,676,641 B2 | 1/2004 | Woodward, Jr. et al. |
| 6,855,129 B2 | 2/2005 | Jenson et al. |
| 6,926,697 B2 | 8/2005 | Malencheck |
| 7,648,483 B2 | 1/2010 | Edwards et al. |
| 7,717,877 B2 | 5/2010 | Lavi et al. |
| 7,799,002 B2 | 9/2010 | Dillard, III |
| 9,028,453 B2 | 5/2015 | Jennings |
| 9,440,026 B2 | 9/2016 | Wozencroft |
| 11,213,631 B2 | 1/2022 | Kim |
| 2002/0010432 A1 | 1/2002 | Klitmose |
| 2005/0171477 A1* | 8/2005 | Rubin ............... A61M 5/326 604/156 |
| 2005/0283120 A1 | 12/2005 | Wang |
| 2010/0083963 A1* | 4/2010 | Wharton ............. A61M 15/009 128/203.15 |
| 2010/0137808 A1 | 6/2010 | Wilmot et al. |
| 2015/0011943 A1 | 1/2015 | Holmes et al. |
| 2016/0184519 A1* | 6/2016 | Blundred ......... A61M 5/16827 604/89 |
| 2018/0126083 A1 | 5/2018 | Schmid et al. |
| 2018/0185584 A1* | 7/2018 | Cowe ................. A61M 5/2455 |
| 2018/0369498 A1* | 12/2018 | Schader ............. A61M 5/3202 |

FOREIGN PATENT DOCUMENTS

| | | |
|---|---|---|
| WO | 91/18634 | 12/1991 |
| WO | 93/13817 | 7/1993 |
| WO | 94/04205 | 3/1994 |
| WO | 95/29721 | 11/1995 |
| WO | WO2013065055 | 5/2013 |
| WO | WO2016210404 | 12/2016 |

OTHER PUBLICATIONS

Examiner's Report for corresponding Canadian Patent Application No. 3,007,875, dated Apr. 11, 2019.

* cited by examiner

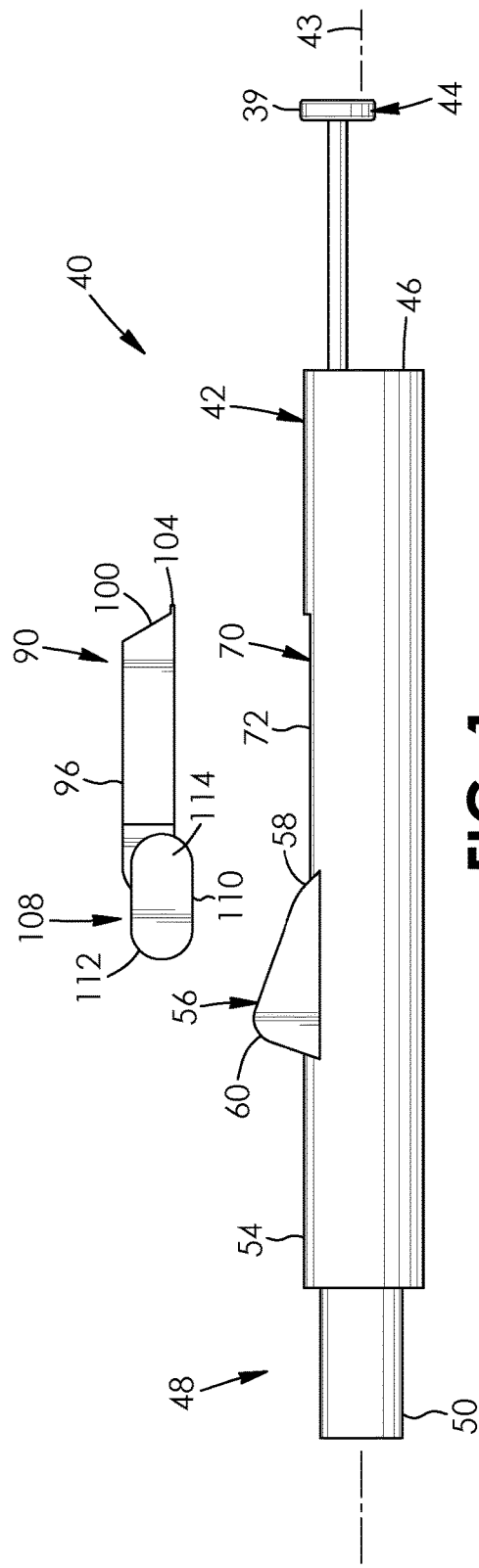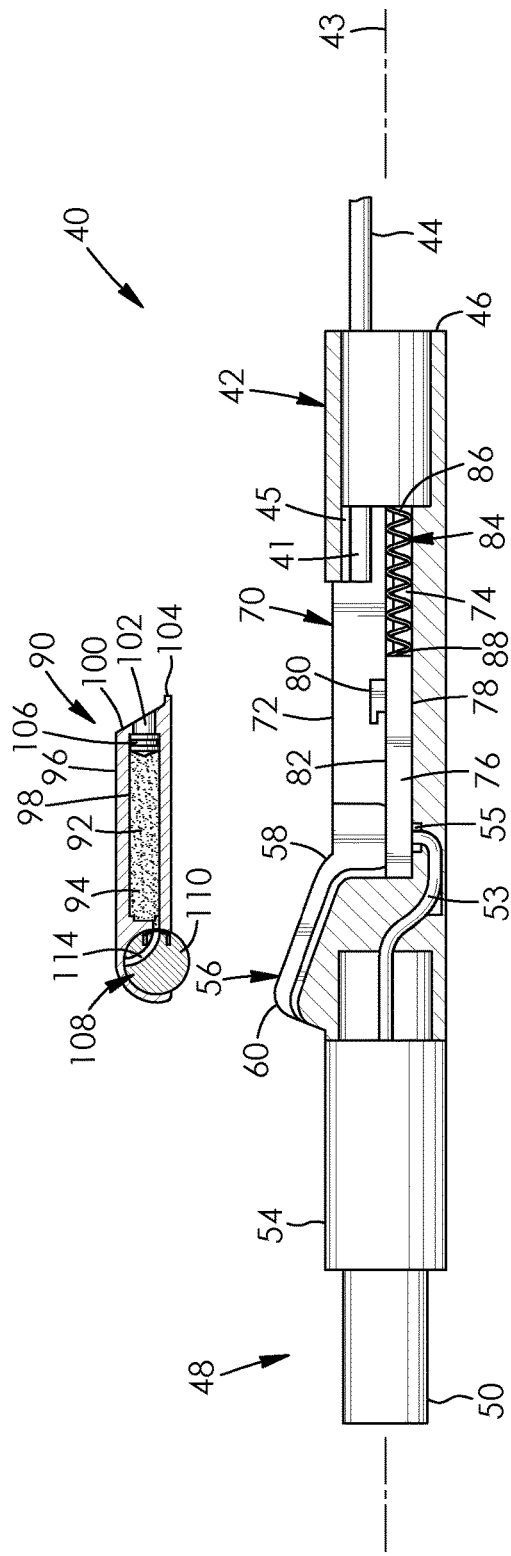

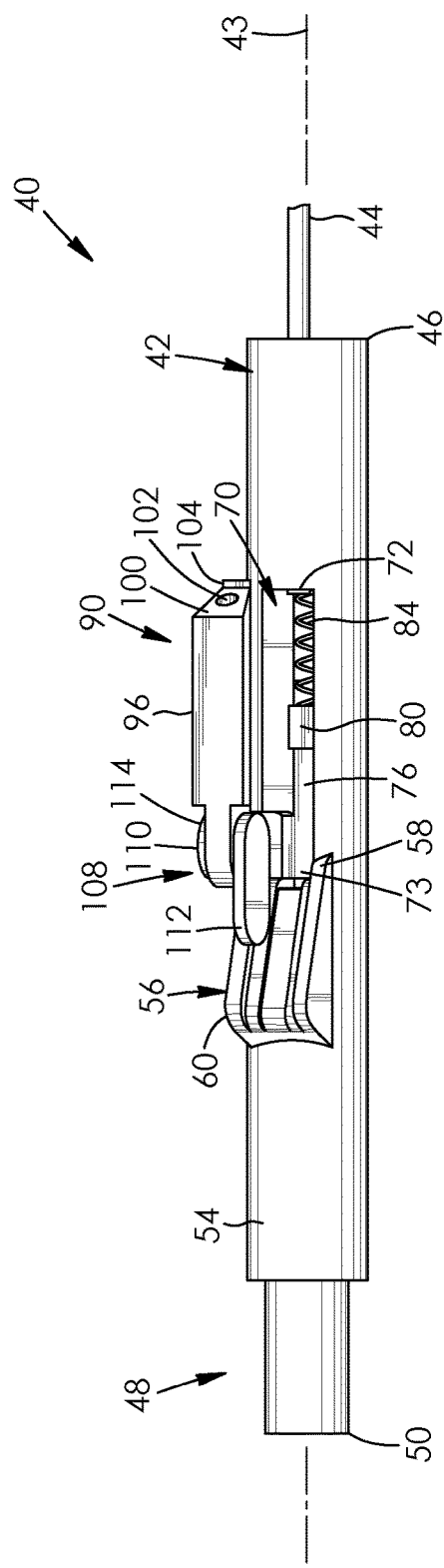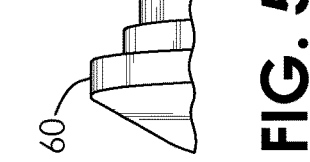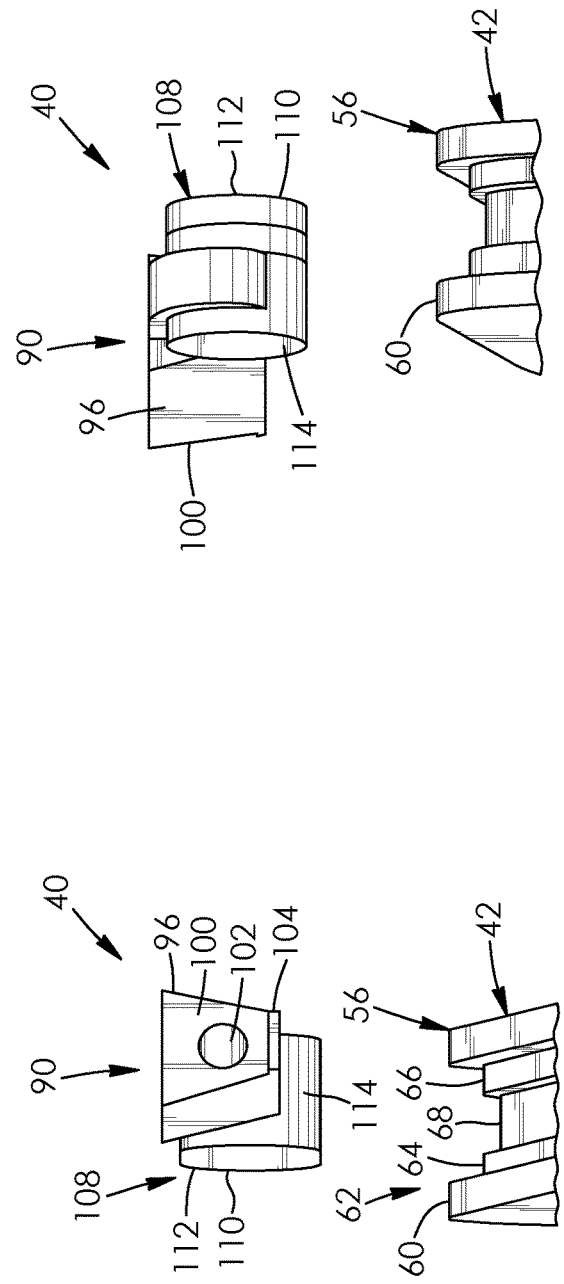

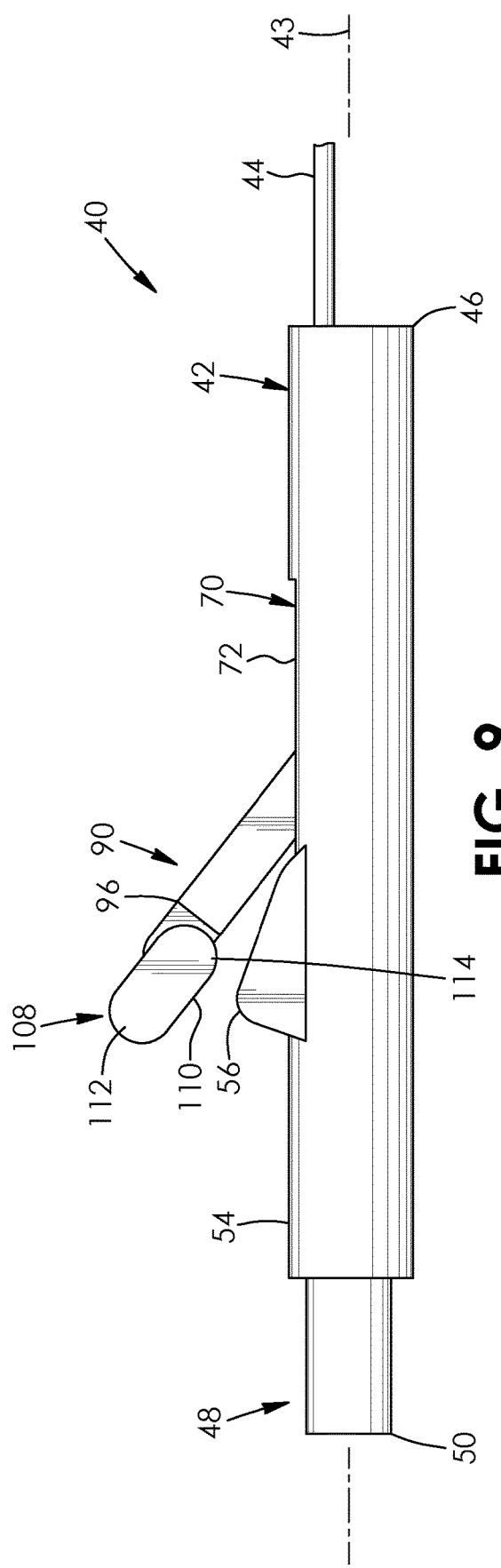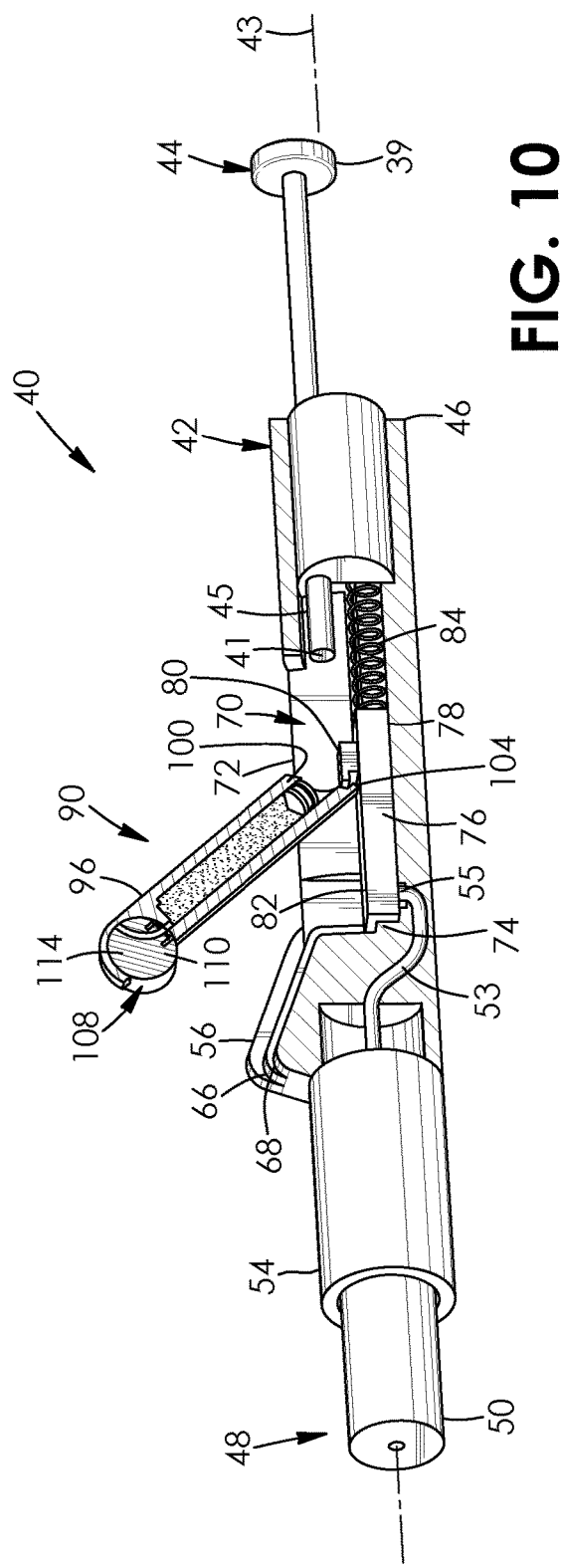

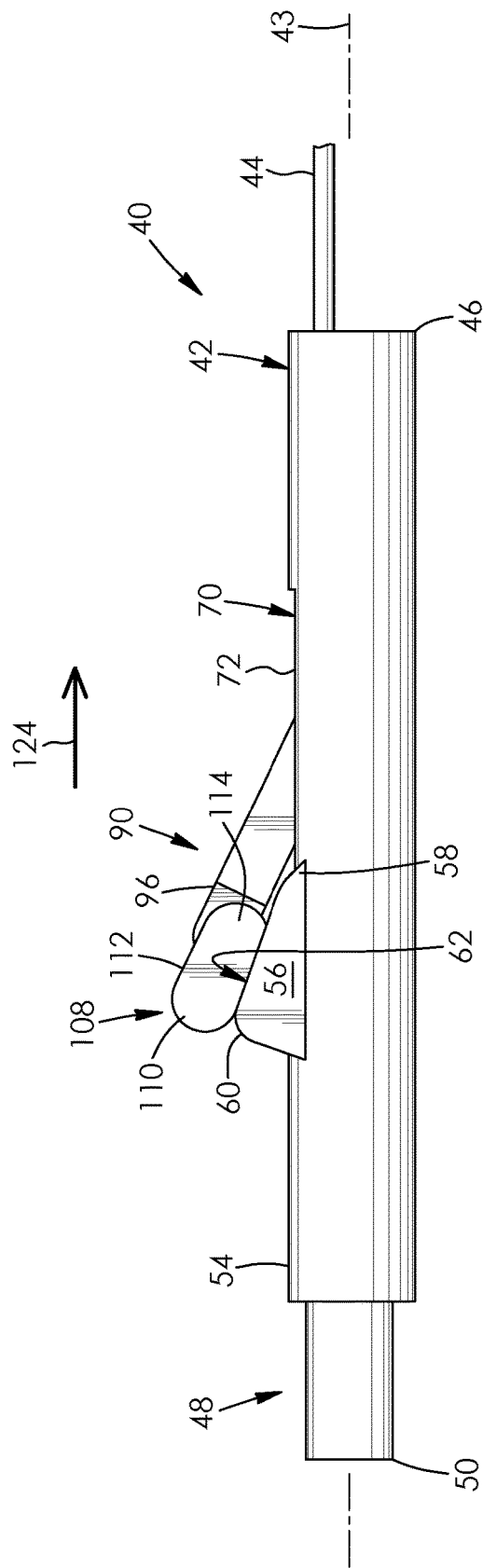
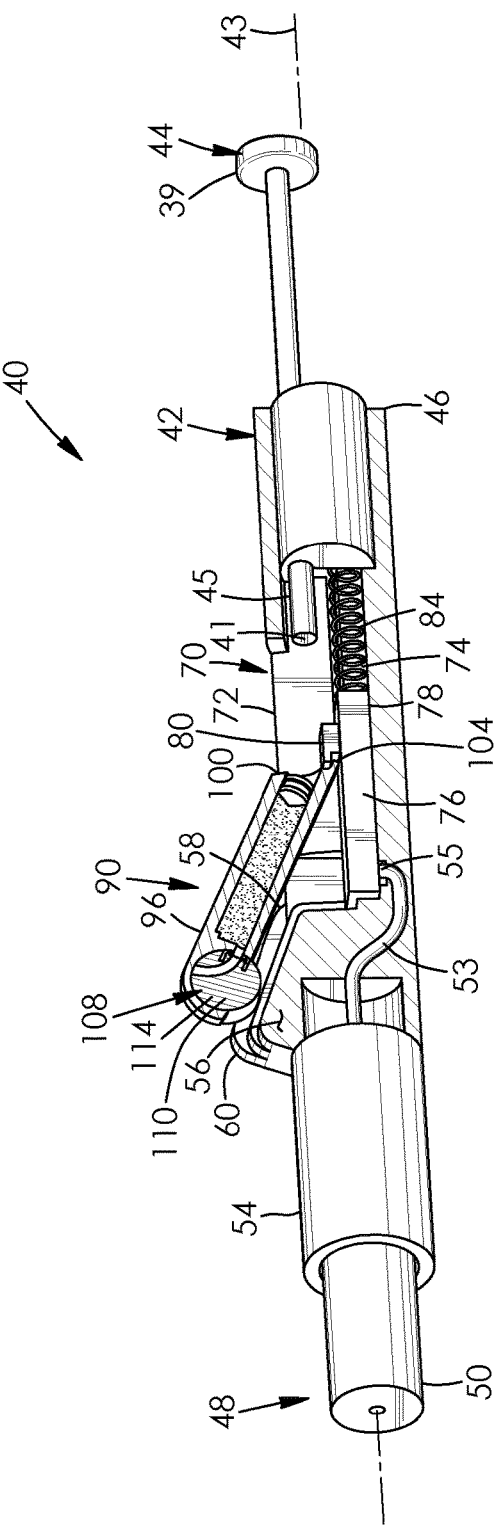
FIG. 11
FIG. 12

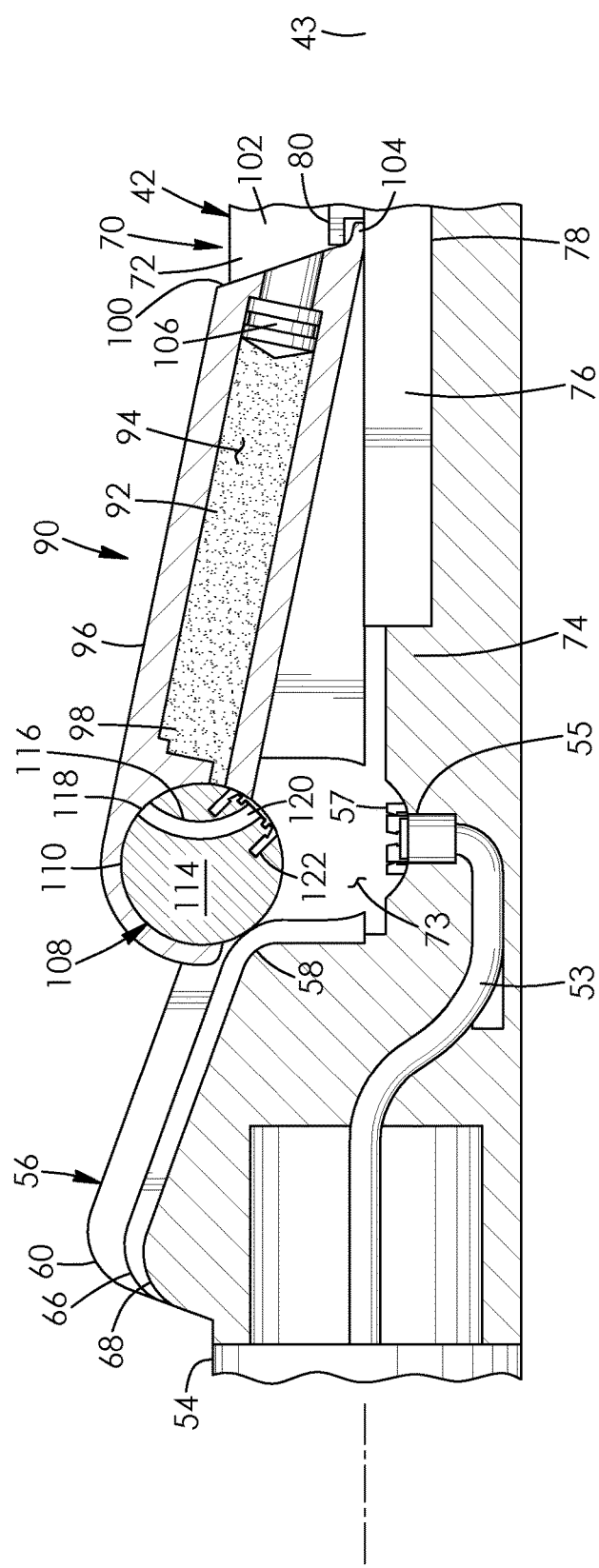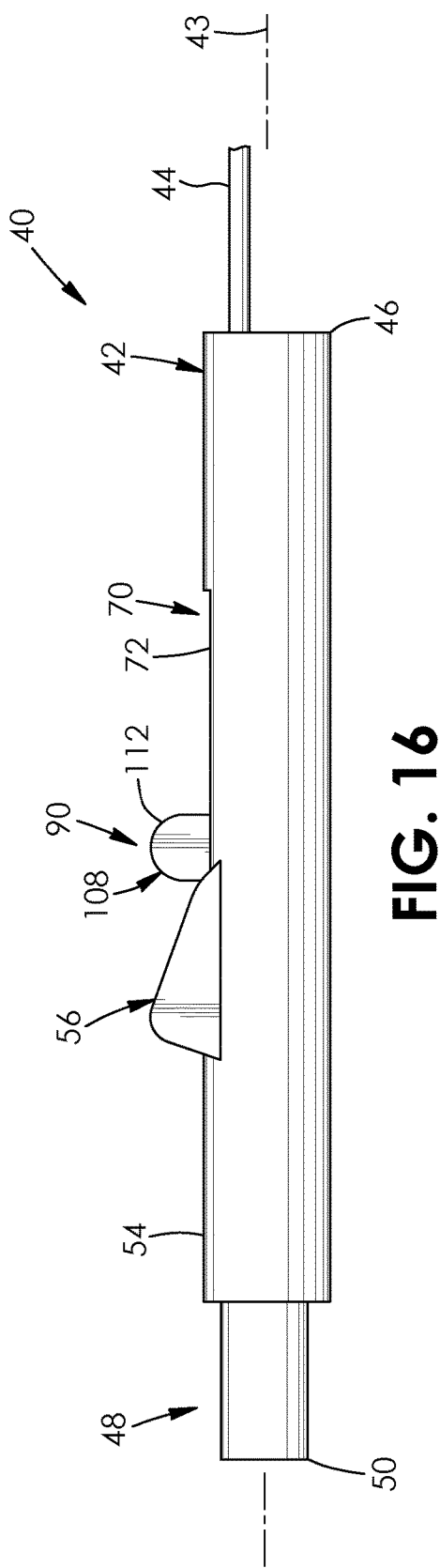

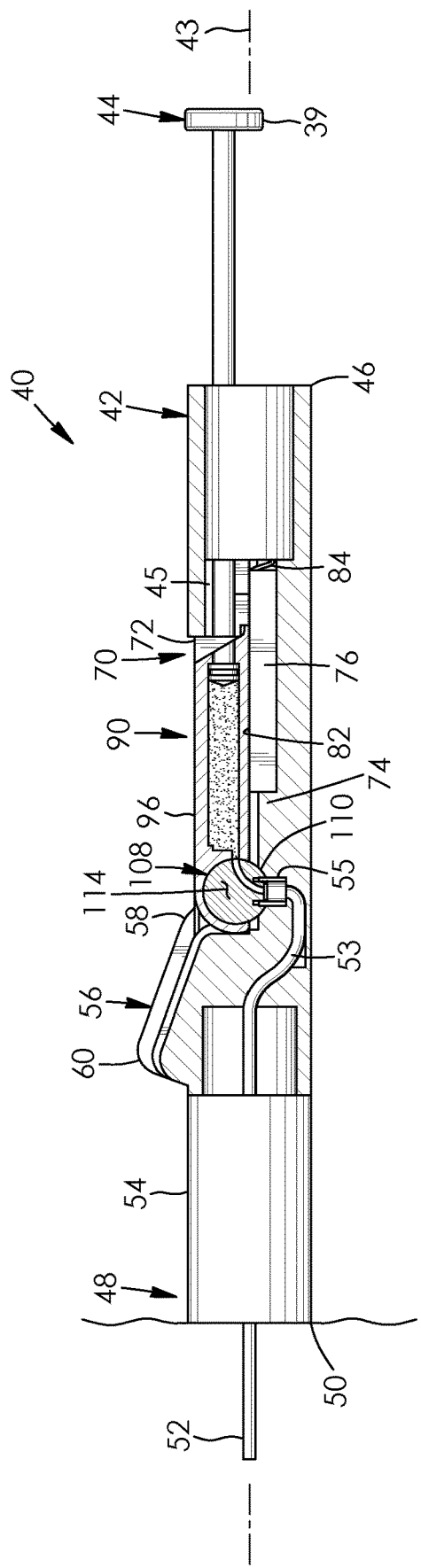
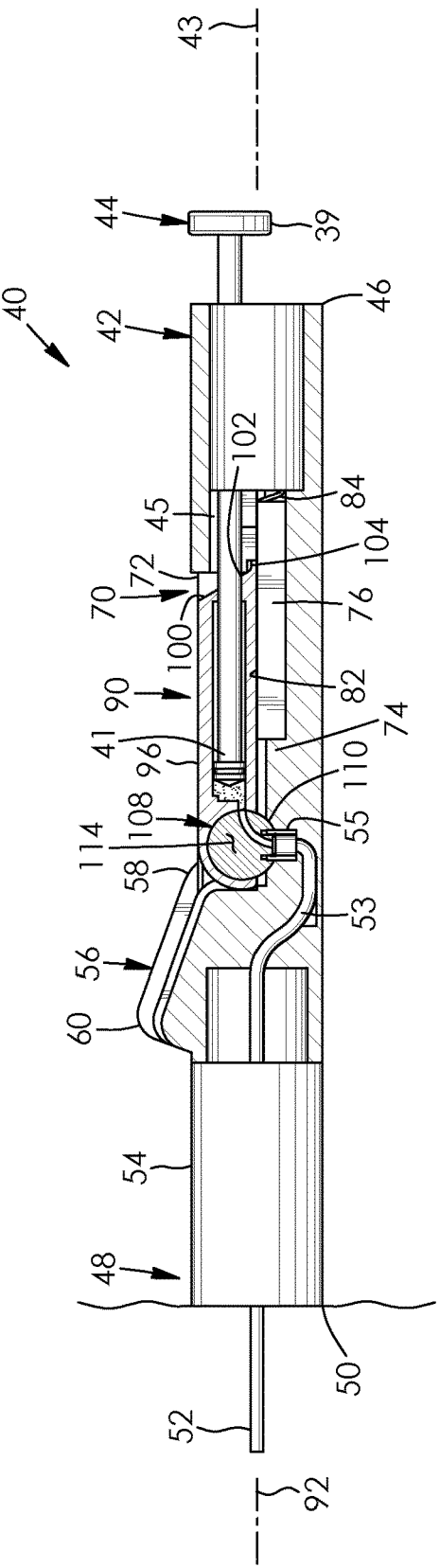
FIG. 18
FIG. 19

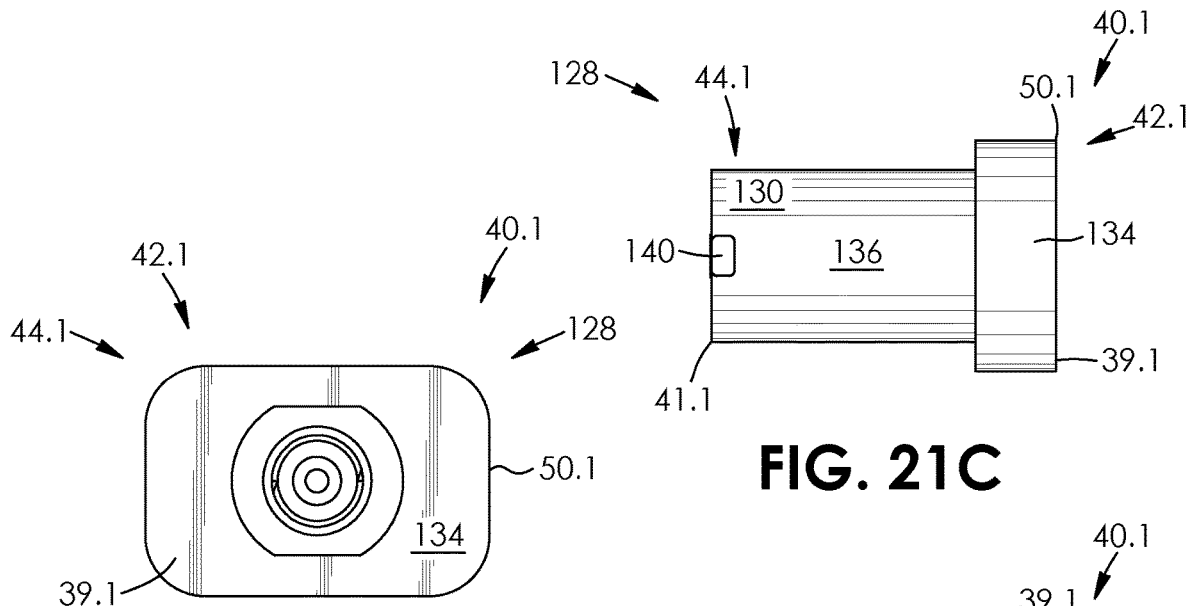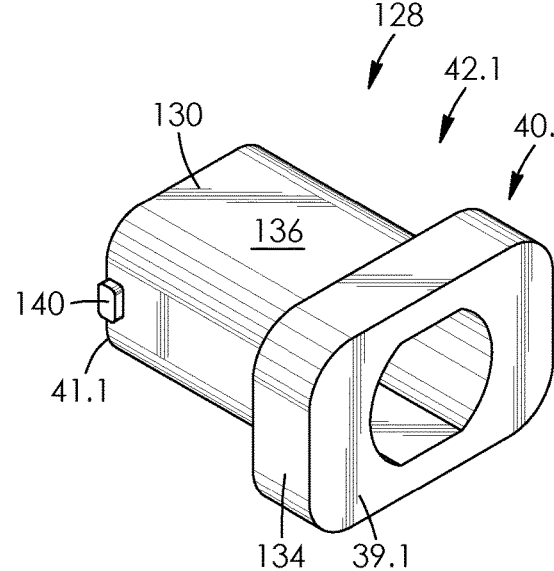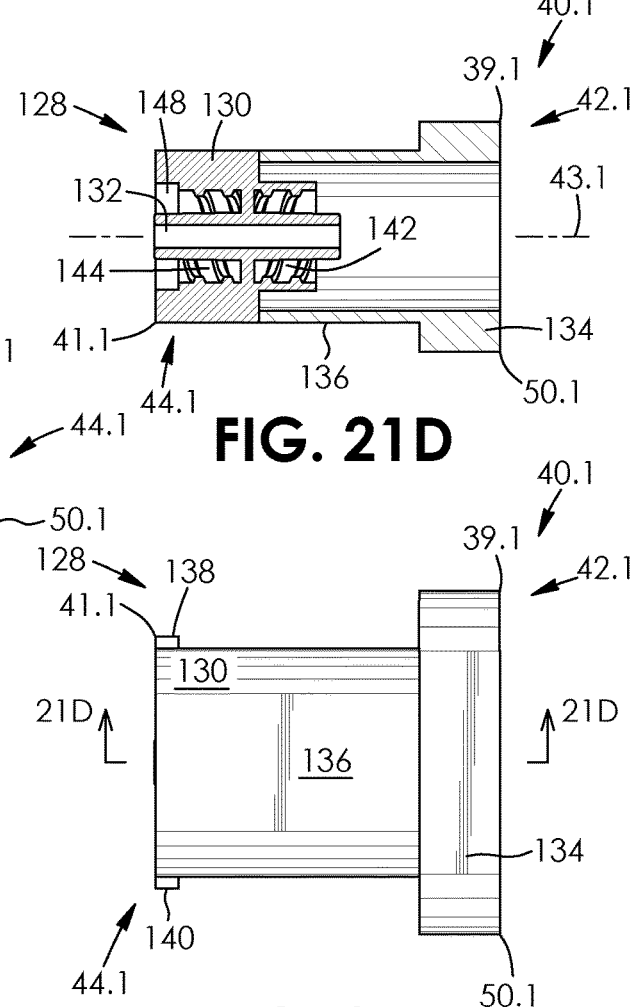

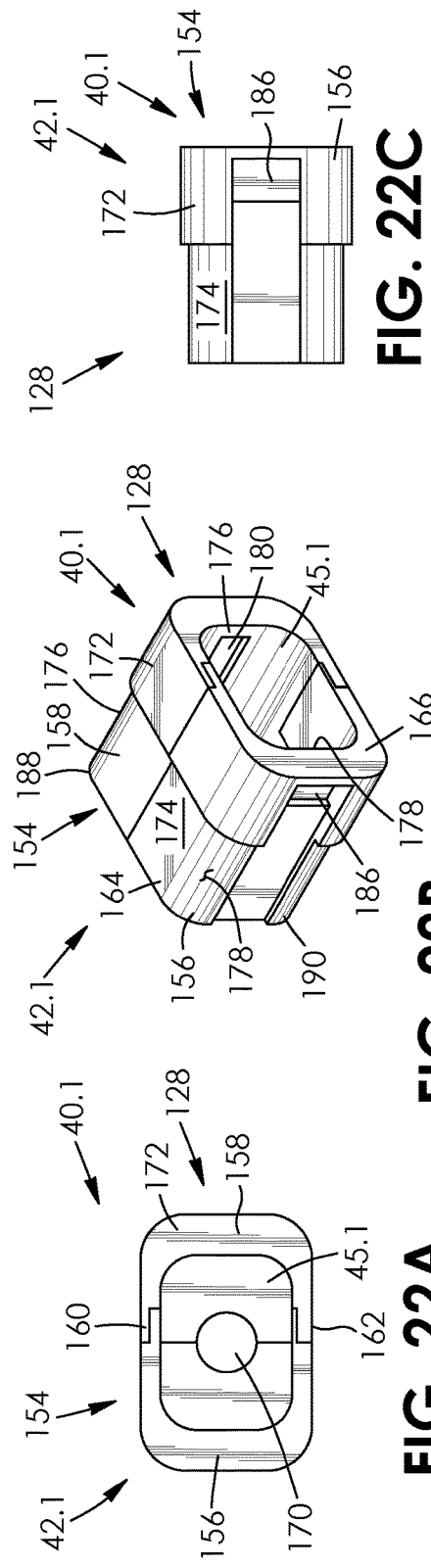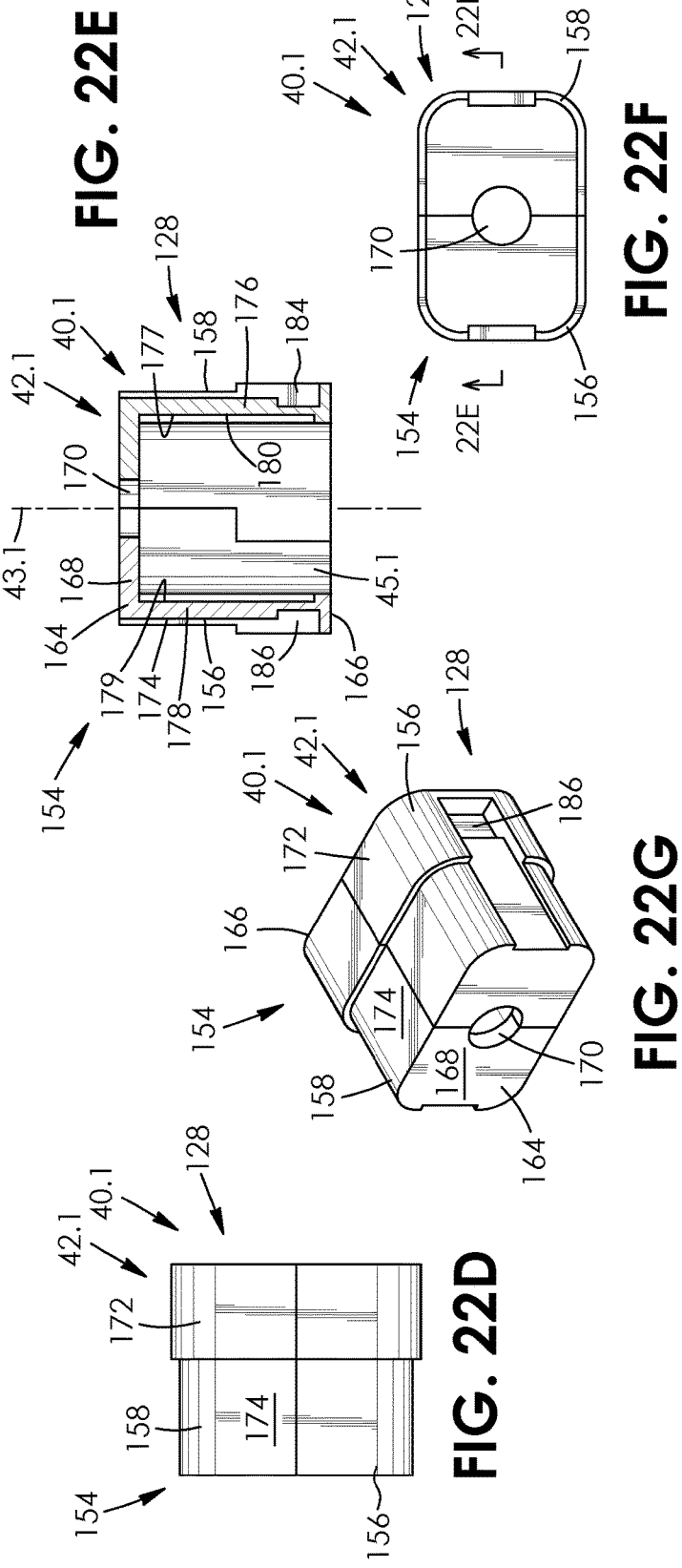

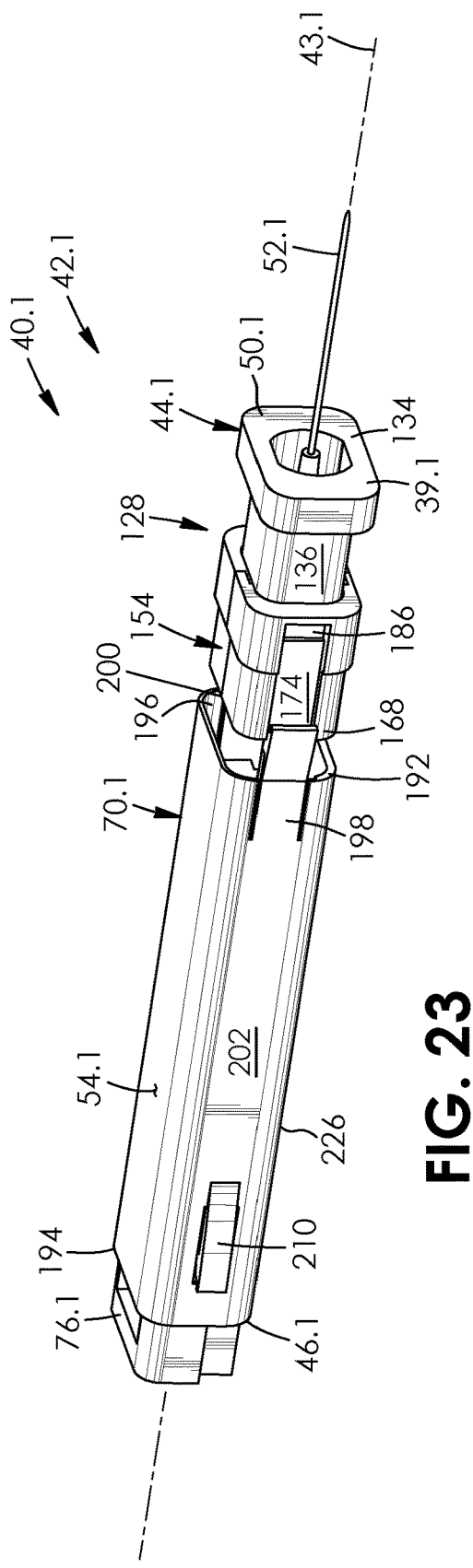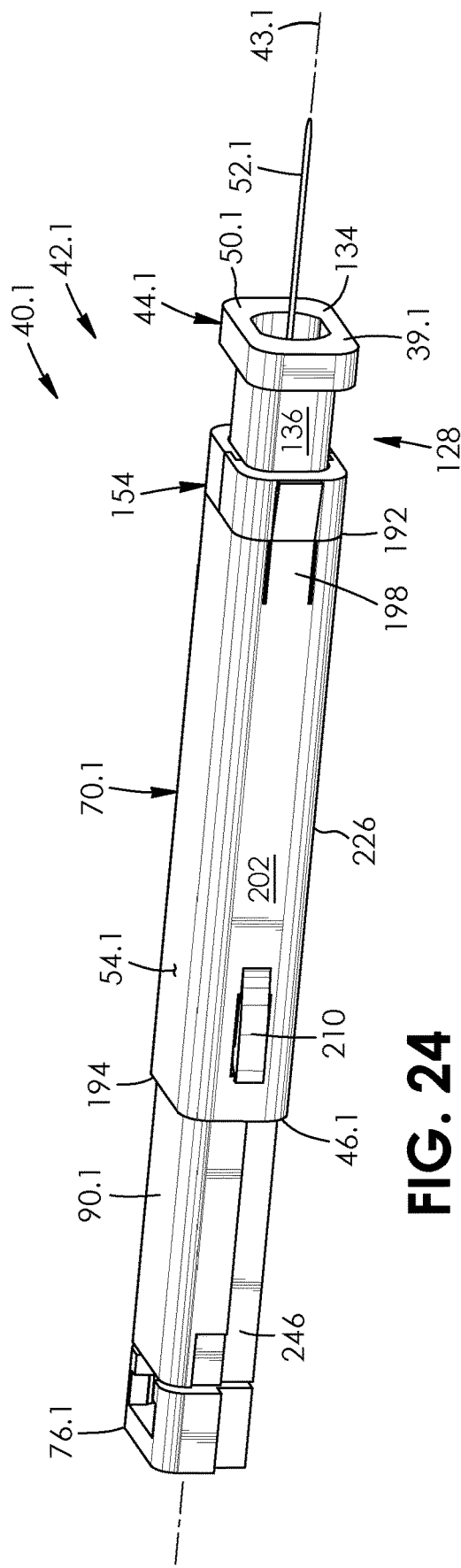

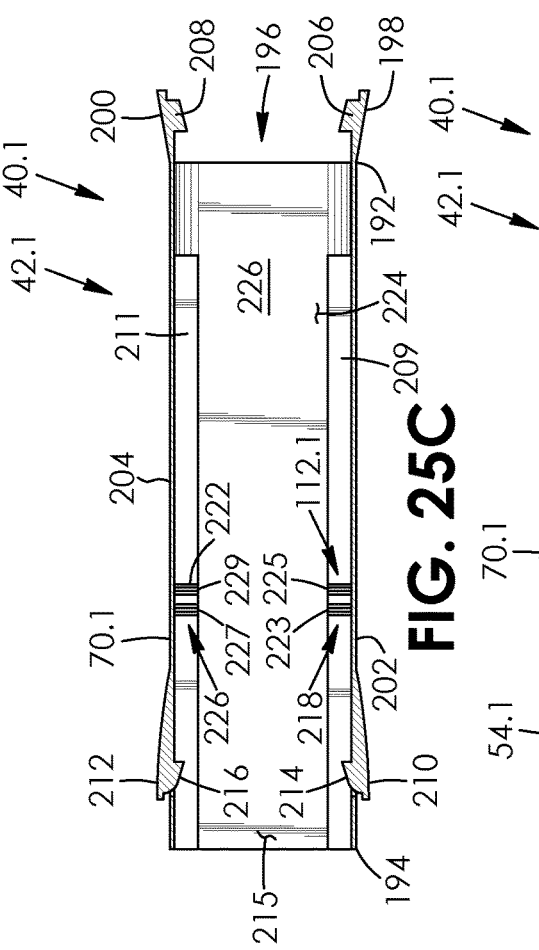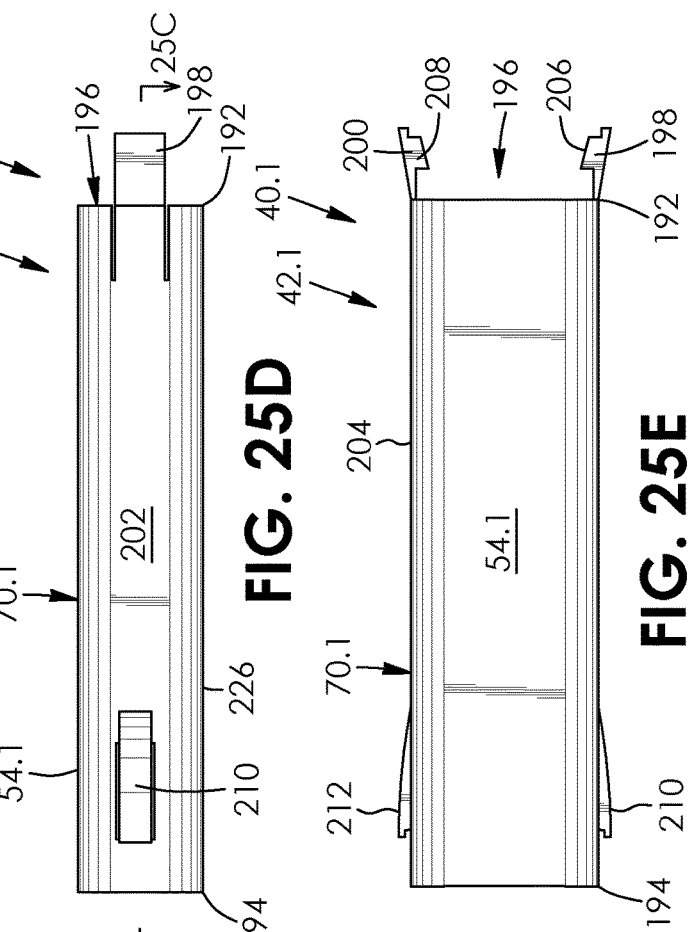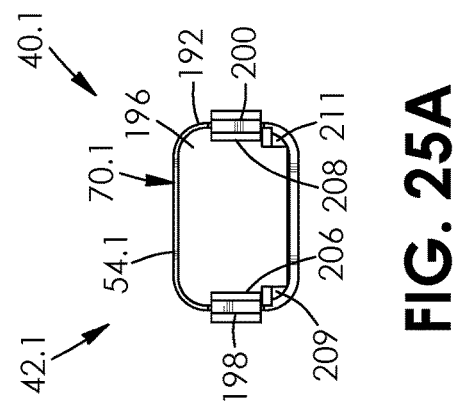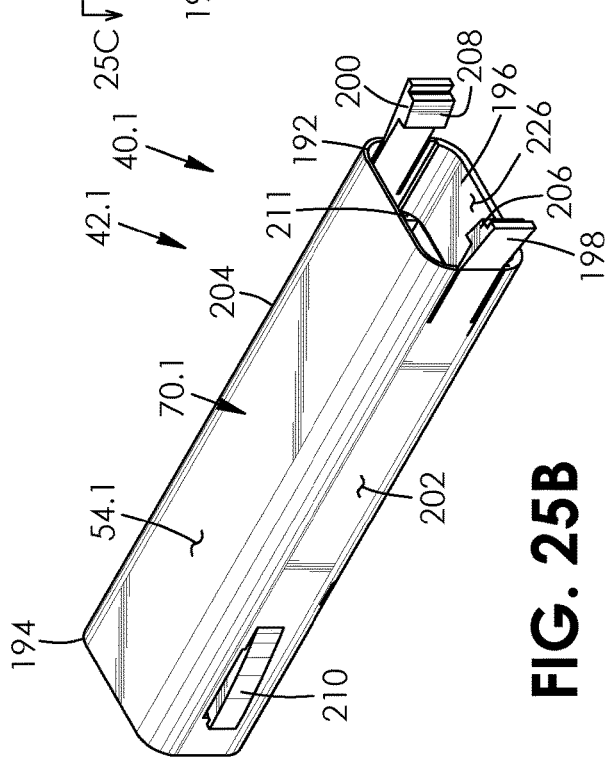

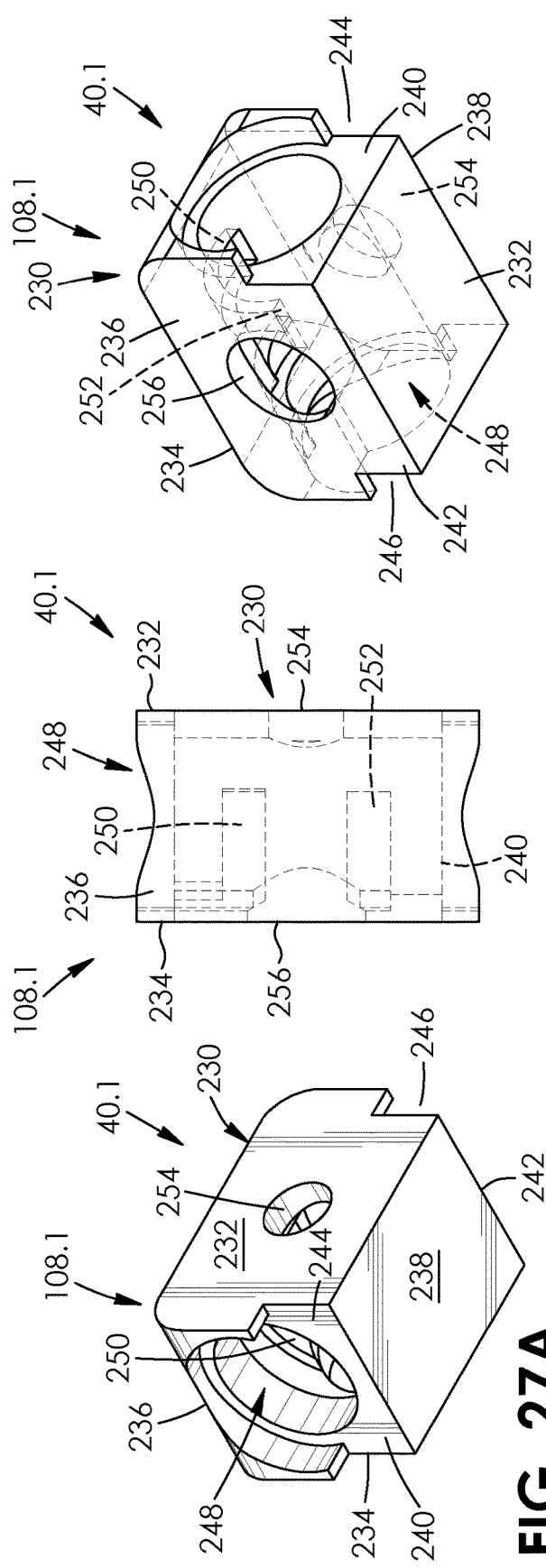
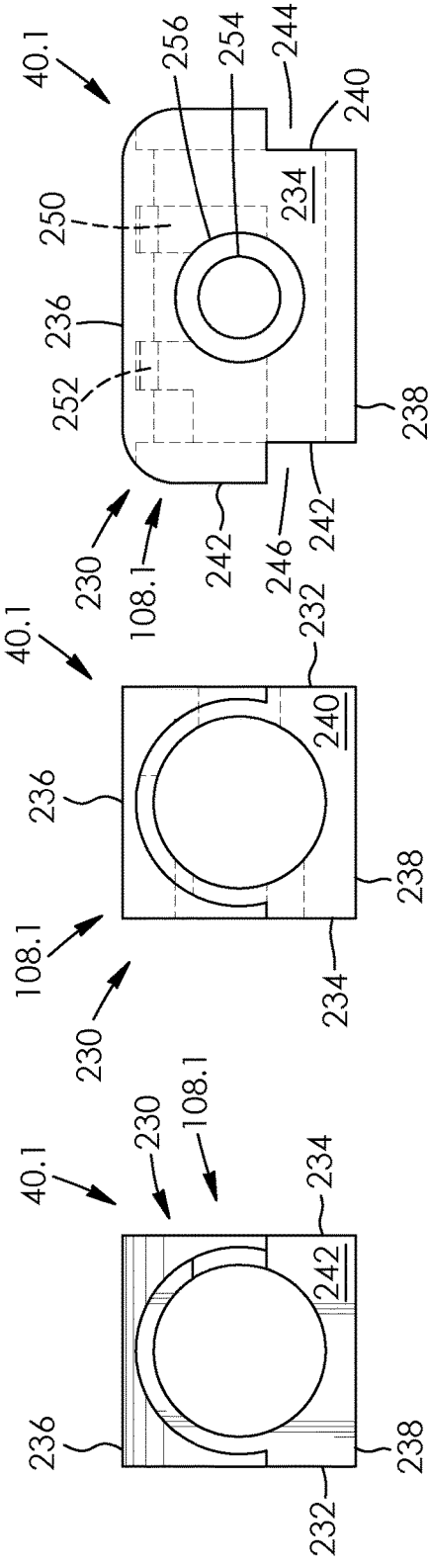

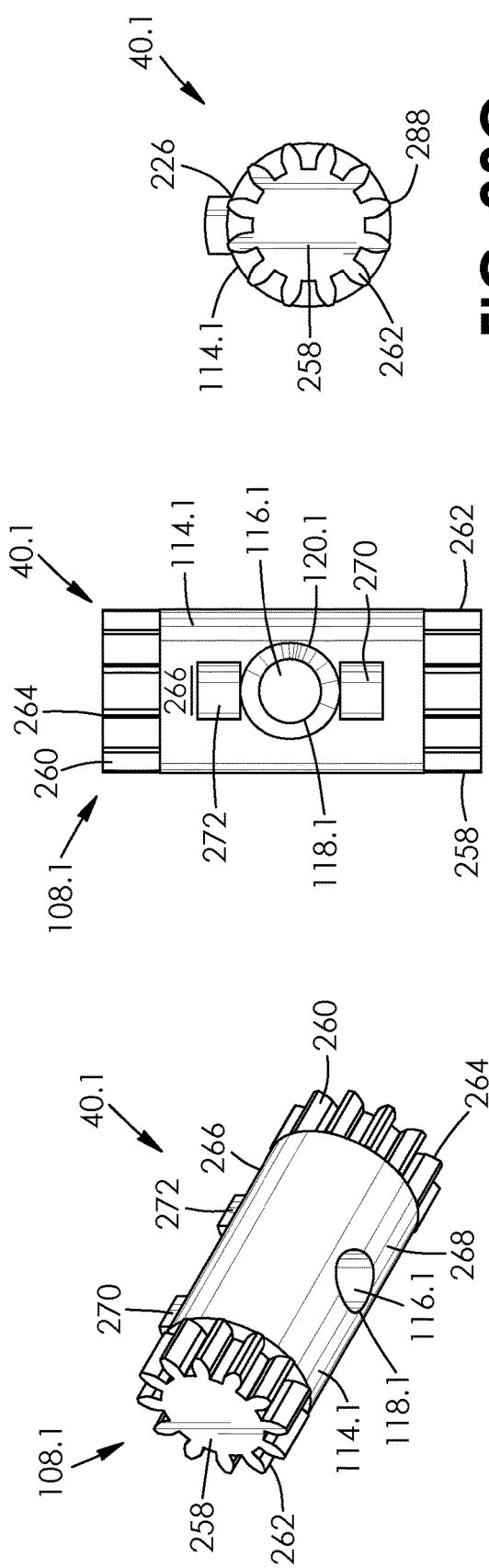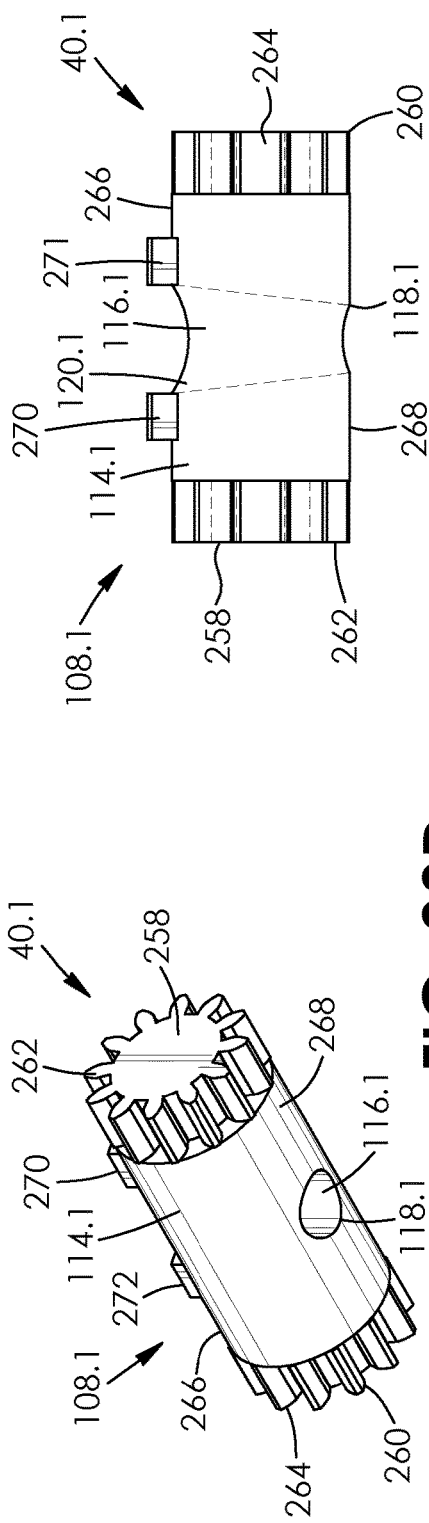

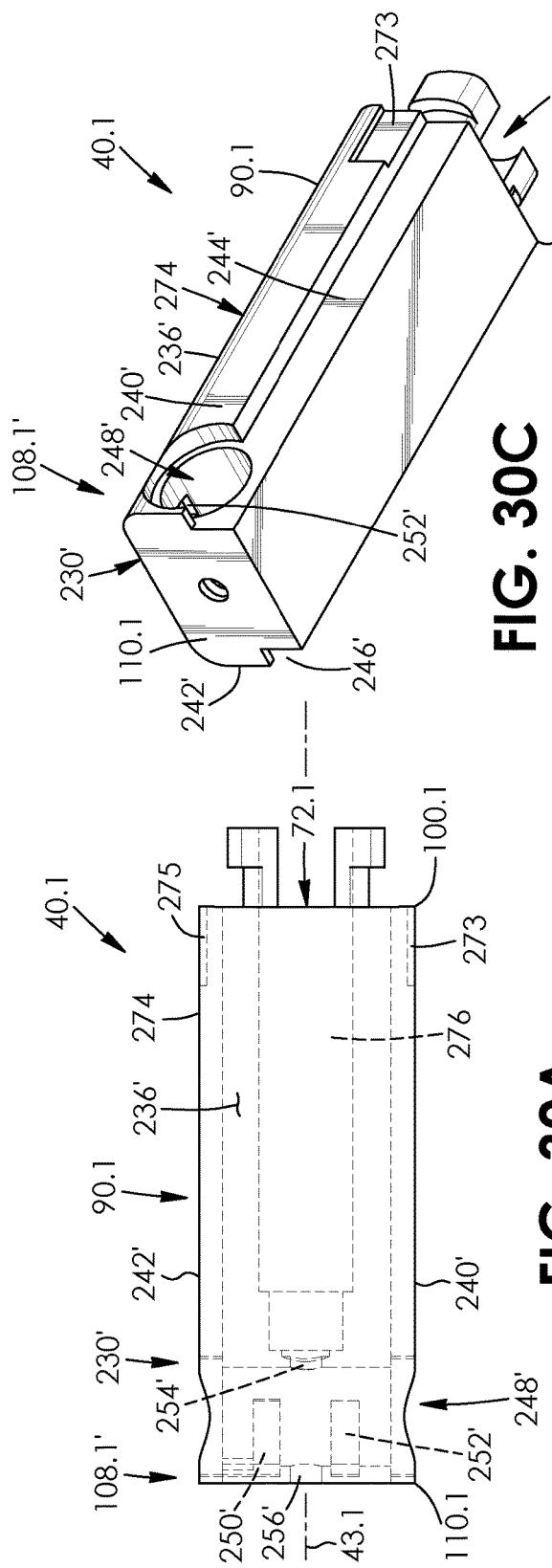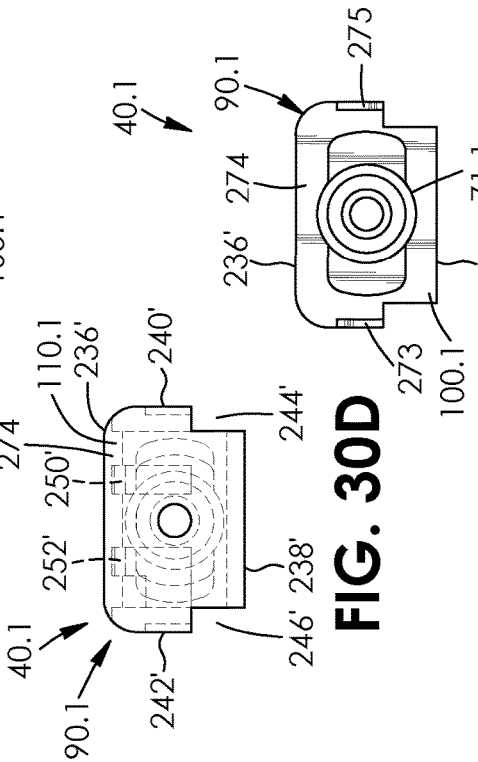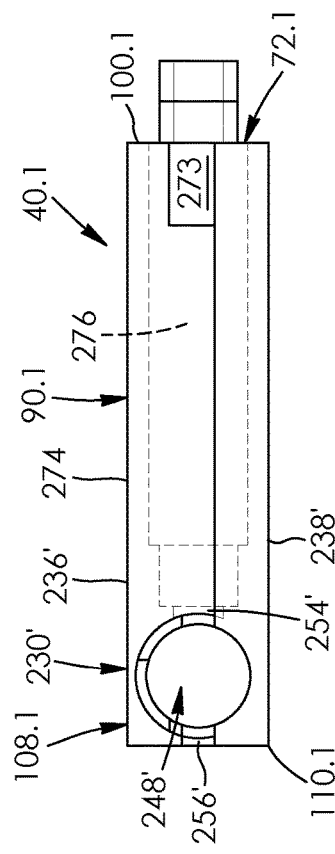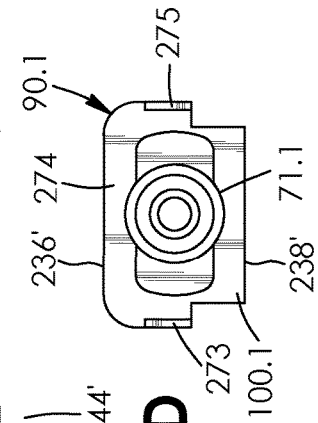

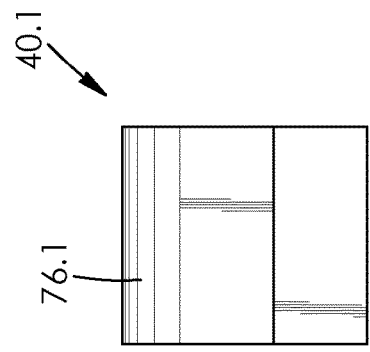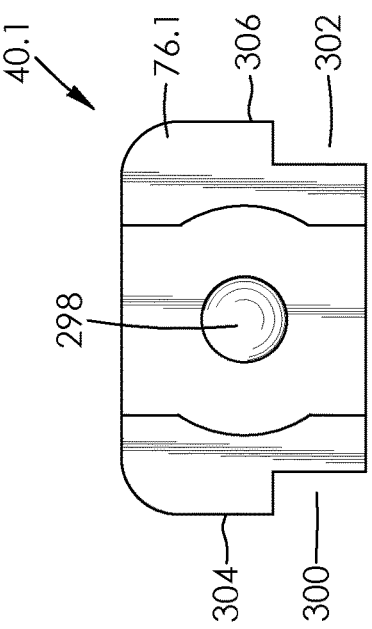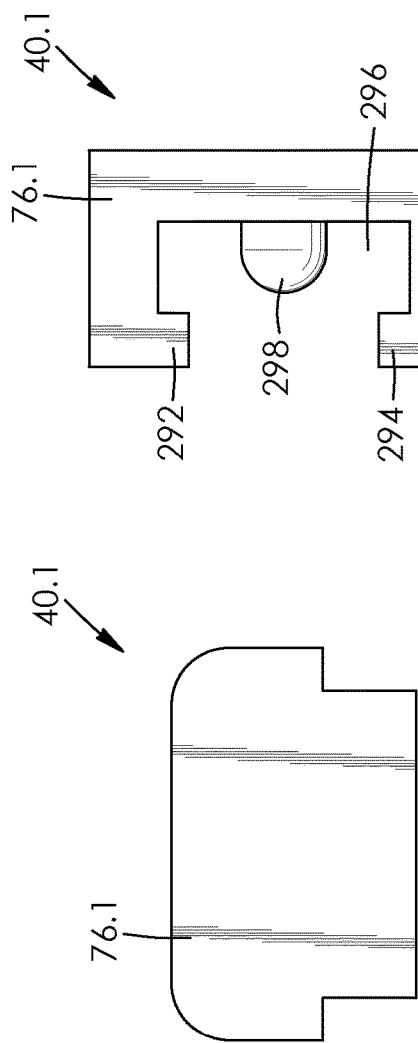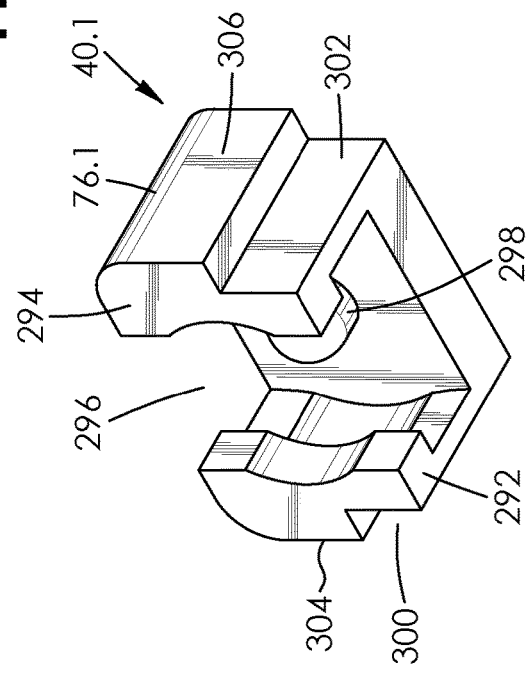

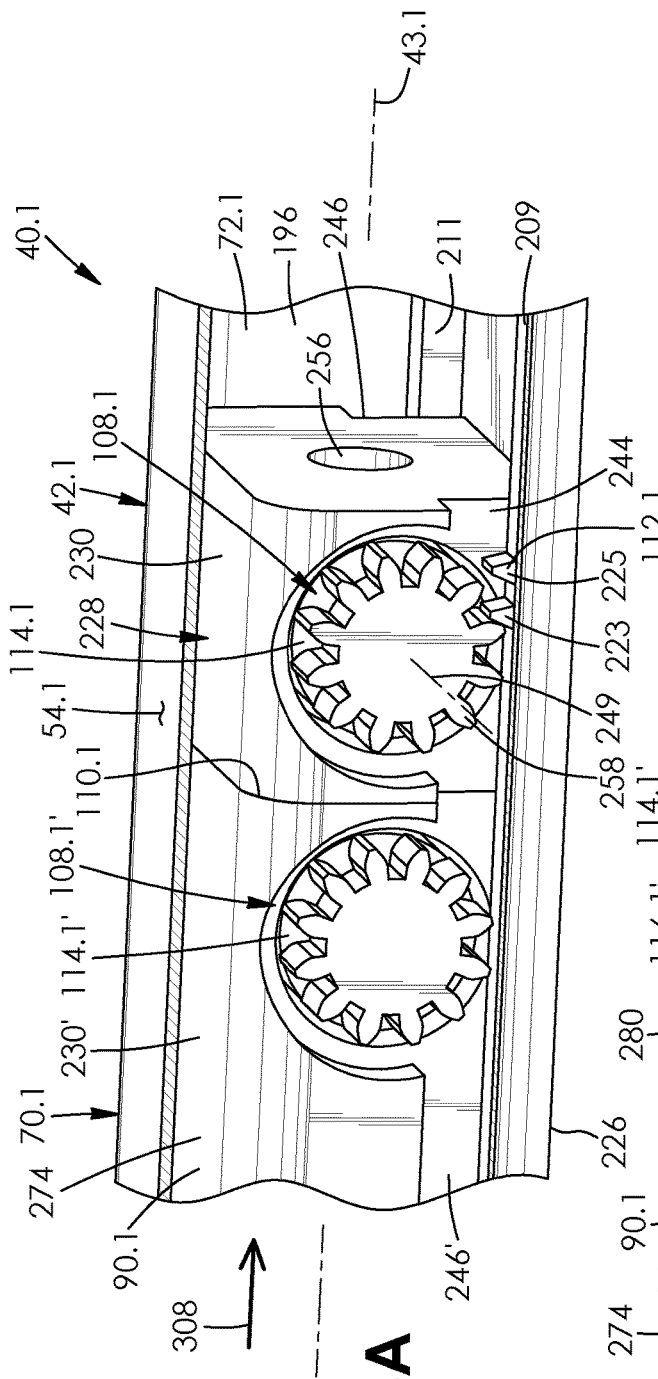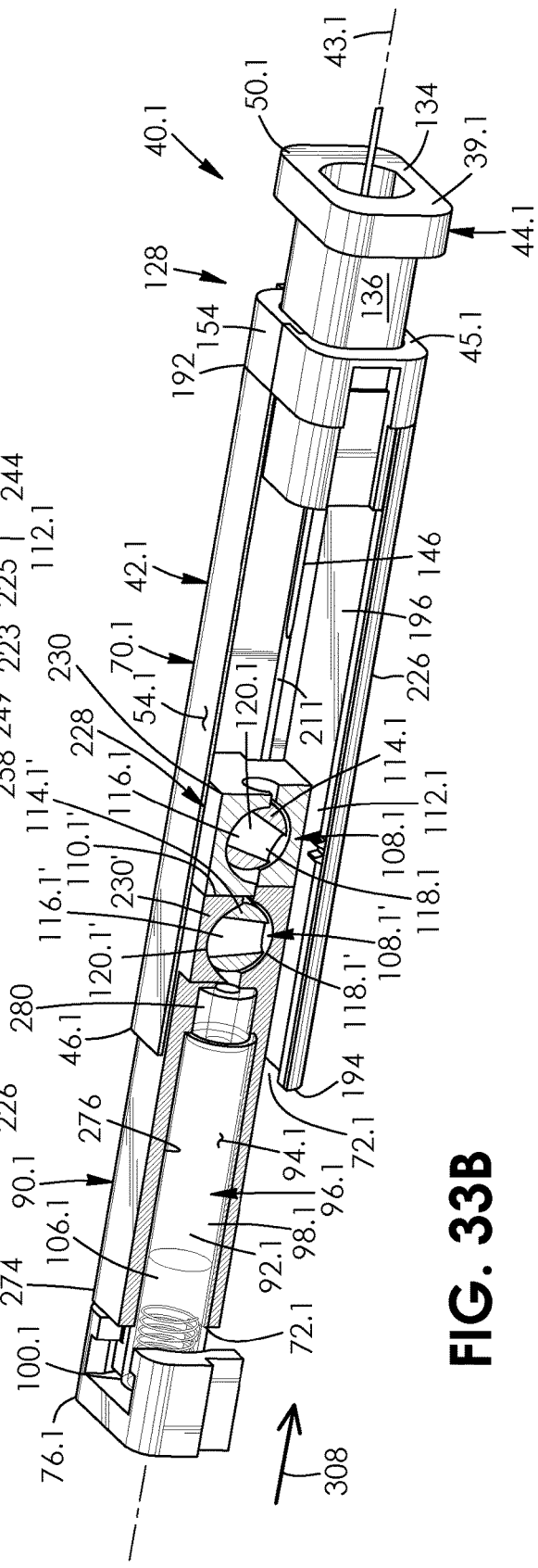

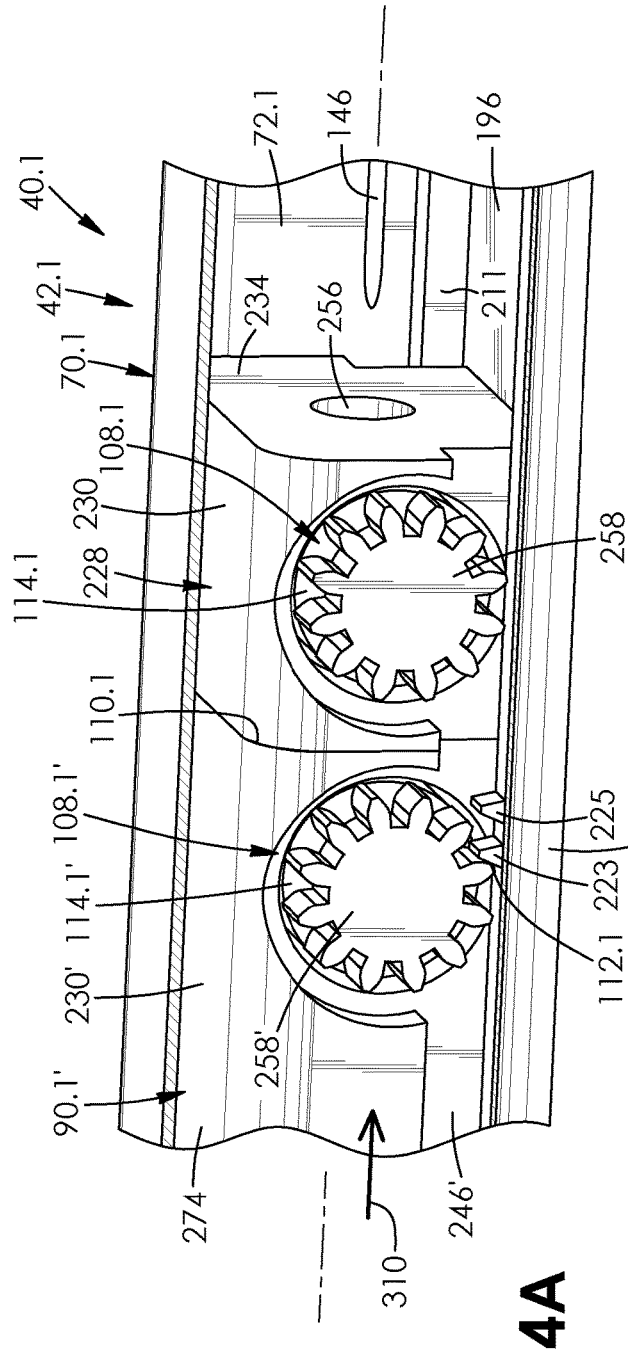
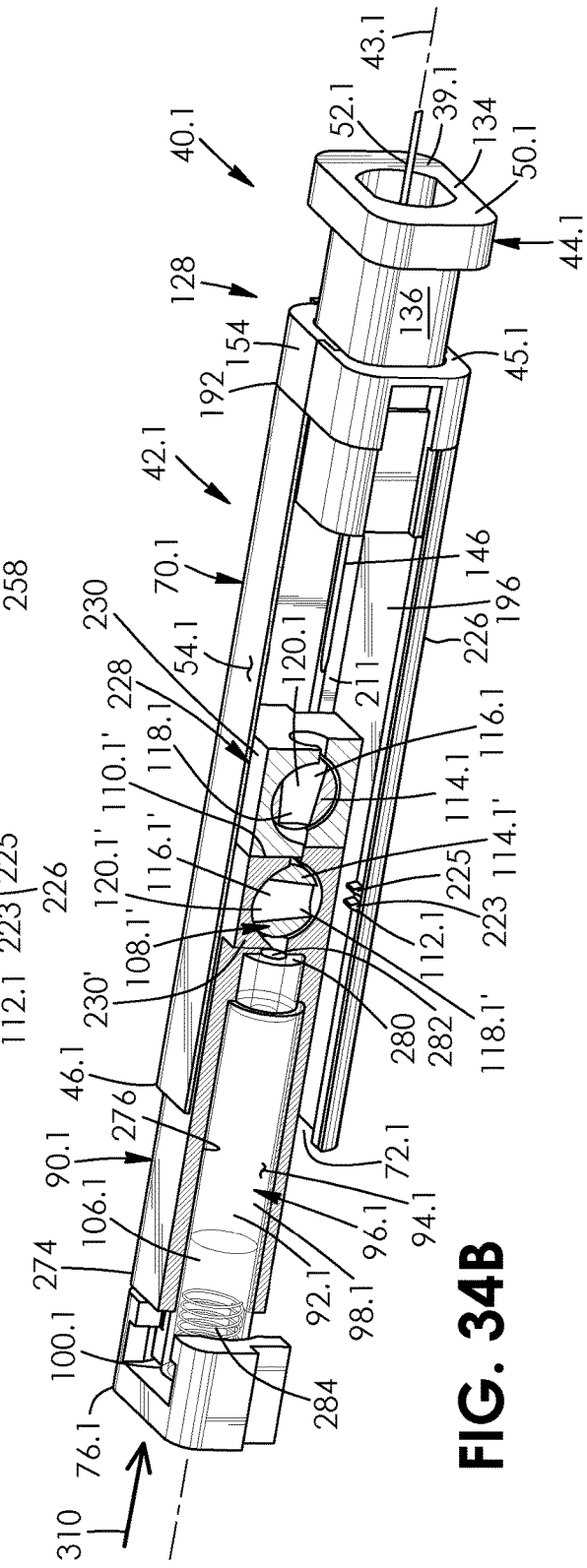
FIG. 34A
FIG. 34B

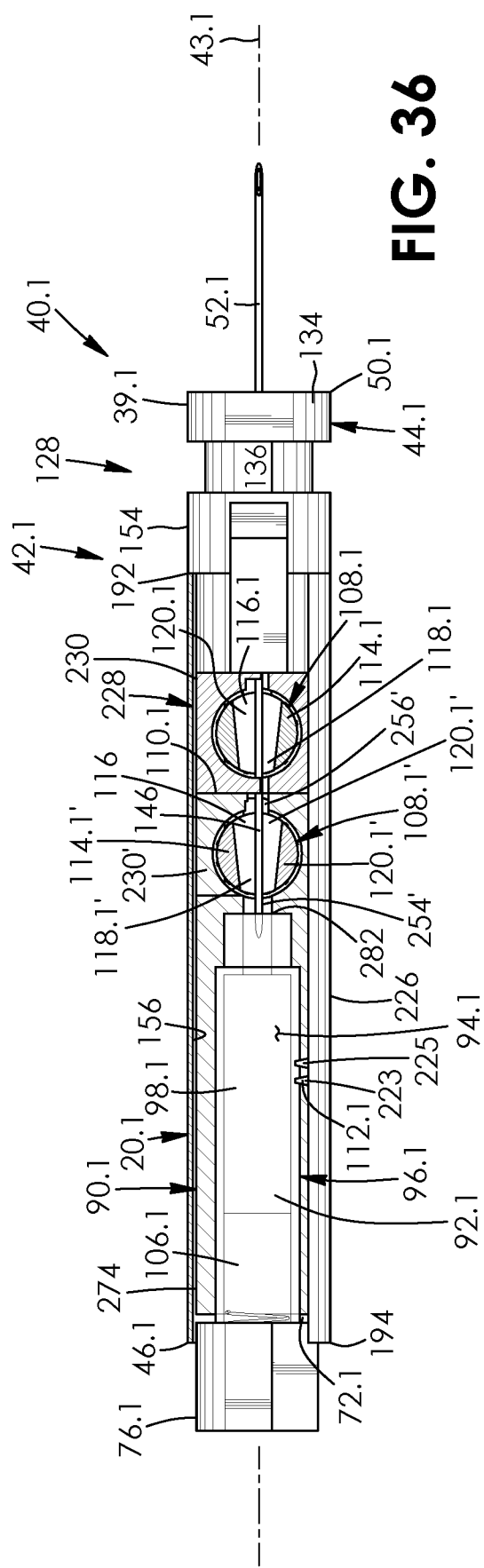
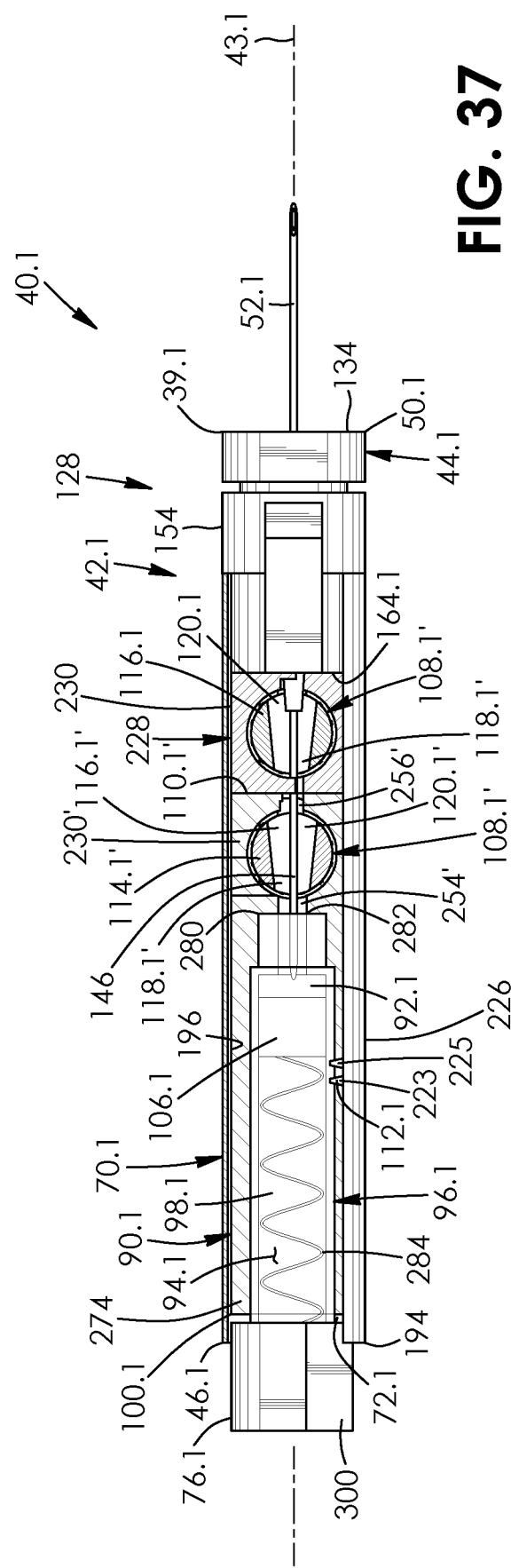

MEDICAMENT INJECTOR AND INTERCHANGEABLE CARTRIDGES THEREFOR

FIELD OF THE INVENTION

The present invention relates to a medicament injector and interchangeable cartridges assembly therefor. In particular, the invention relates to a medicament injector configured to selectively receive various interchangeable medicament-carrying cartridges.

DESCRIPTION OF THE RELATED ART

United States Patent Application Publication No. 2018/0126083A1 to Schmid et al. discloses an adjustable injection device for administering a substance. The device includes a housing with an array of fastening points and at least two housing-like shells, each having at least one holding device and at least one blocking device for attaching to the housing. The holding device of a first shell can be attached to a fastening point, and the holding device of a second shell can be attached to a further fastening point. The holding device of the first shell is prevented from disengagement therefrom by the blocking device of the second shell, and the holding device of the second shell is prevented from disengagement therefrom by a blocking device of a further shell, or, in the event that the injection device has only two shells, is prevented from disengagement from the further fastening point by a blocking device of the first shell whereby the shells are non-detachably connected to the housing.

International Patent Application Publication No. WO 2013/065055 A1 to Lev discloses an electronic autoinjector apparatus for use with a replaceable pre-filled cassette containing liquid contents for administrating a liquid drug to a patient. The electronic autoinjector apparatus includes a handheld pen-like electronic autoinjector having an autoinjector housing with an open ended cassette holder for manual sliding installation of a cassette therein and sliding removal therefrom. The electronic autoinjector apparatus also includes a remote control unit having a base with a storage cavity for snugly receiving the electronic autoinjector when not in use and a cover for closing the base, and a user control interface for operating the electronic autoinjector apparatus.

International Patent Application Publication No. WO 2016/210404 A1 to Lev discloses an injector assembly for automatically delivering a dose of a medicament to a subject. The assembly includes an activation switch for initiating automatic delivery of the dose of the medicament. The assembly includes a needle aperture at a distal end of the injector assembly configured for a needle to pass therethrough. The assembly includes a plunger drive mechanism for applying pressure to a plunger assembly, the plunger drive mechanism including a motor operably connected to the activation switch, and an actuator operably connected to the motor and the plunger assembly. The assembly includes a surface for operatively connecting to at least a portion of a removable cartridge module, the removable cartridge module including: a needle housing for dictating a range of injection depths possible. The assembly includes a plunger housing for aligning the plunger assembly with the plunger drive mechanism. The assembly includes an identification element containing a code associated with a pre-filled cartridge and/or medicament contained within, and a cavity for reversibly securing the pre-filled cartridge. The assembly includes at least one engagement feature for securing the removable cartridge module to the surface. The assembly includes a cartridge drive assembly for moving the pre-filled cartridge axially between the proximal and distal end of the injector assembly, the cartridge drive assembly including at least one gear element operably connected to the motor and the activation switch.

Giving medicines is cumbersome as it requires multiple components and multiple steps to draw up the medication into the syringe and deliver to the patient via an injection with needle. The steps involved to deliver the medication include utilization of the syringe/plunger, needle, and medication combination. The clinical provider must draw up the right medication at the dose appropriate for each patient and clinical situation. Further, the common delivery routes include IM (Intramuscular) and IV (Intravenous) routes. Given the complexities and various steps involved, this can cause significant time delay and operational errors that can have detrimental outcomes for patients. In a non-hospital clinical setting such as pre-hospital/transport medicine, aerospace medicine, bystander first-aid, and military medicine, the advantage of reduced bulk/components, versatility, and ease of use is also critical. There may accordingly be a need for an employed medicament injector with interchangeable medicament cartridges.

BRIEF SUMMARY OF INVENTION

The present invention provides, and it is an object to provide, an improved medicament injector and interchangeable cartridges therefor.

There is accordingly provided a medicament injector according to a first aspect. The medicament injector includes an applicator with a cartridge-accepting receptacle. The medicament injector includes an interchangeable cartridge with a body shaped to receive or contain a medicament within an interior thereof. The cartridge includes at least one barrier member having a closed position in which access to the medicament is inhibited. The barrier member is moveable from the closed position to an open position, in which the medicament is accessible via the applicator, when the cartridge is inserted into the cartridge-accepting receptacle. The barrier member moves back to the closed position when the cartridge is removed from the cartridge-accepting receptacle.

There is also provided a medicament injector according to a second aspect. The medicament injector includes an applicator with a cartridge-accepting receptacle. The medicament injector interacts with an interchangeable cartridge with a body shaped to receive or contain a medicament within an interior thereof. The cartridge includes a valve coupled to the body. Insertion of the cartridge into the cartridge-accepting receptacle actuates the valve to move from a closed position, in which access to the medicament is inhibited, to an open position in which the medicament is accessible via the applicator.

There is further provided a medicament injector according to a third aspect. The medicament injector includes a needle. The medicament injector includes a cartridge-accepting receptacle coupled to the needle. The medicament injector includes an interchangeable cartridge having an interior in which a medicament is prefilled, contained or received. The cartridge has a pre-injection mode in which access to the medicament is inhibited. Insertion of the cartridge into the cartridge-accepting receptacle causes the cartridge to move from the pre-injection mode to an injection mode in which the medicament is accessible via the needle.

There is additionally provided a kit comprising a plurality of interchangeable cartridges with variable medicaments and one of the above set out medicament injectors.

There is yet further provided a medicament injector according to a fourth aspect. The medicament injector includes an applicator with a cartridge-accepting receptacle. The medicament injector includes a plurality of interchangeable cartridges containing pre-filled amounts of one or more medicaments therewithin. The medicament injector includes a reversible barrier mechanism which inhibits access to the medicament until a selected one of said cartridges is inserted into the cartridge-accepting receptacle.

BRIEF DESCRIPTION OF DRAWINGS

The invention will be more readily understood from the following description of preferred embodiments thereof given, by way of example only, with reference to the accompanying drawings, in which:

FIG. 1 is a side elevation view of a medicament injector according to one embodiment, the medicament injector comprising an applicator and an interchangeable medicament-carrying cartridge positioned above the applicator, the applicator including a plunger adjacent to a first end thereof and a protective needle assembly extending about a needle (not shown) adjacent to a second end thereof, the cartridge including a hollow body and a valve pivotally coupled to the body, with the valve including a valve actuator shown in a closed position;

FIG. 2 is a side elevation view of the medicament injector of FIG. 1, with the applicator and the cartridge being shown in section to reveal the interior thereof;

FIG. 3 is a top, side perspective view of the medicament injector of FIG. 1;

FIG. 4 is a perspective view of the cartridge of FIG. 1 shown from a plunger-input end thereof, together with a cartridge-accepting receptacle of the applicator of FIG. 1 shown in fragment;

FIG. 5 is a perspective view of the cartridge of FIG. 1 shown from a valve actuator end thereof, together with the cartridge-accepting receptacle of the applicator of FIG. 1 shown in fragment;

FIG. 9 is a side elevation view of the medicament injector of FIG. 1, with the cartridge shown in the process of being inserted within the cartridge-accepting receptacle of the applicator via the plunger-input end of the cartridge;

FIG. 10 is a side perspective view of the medicament injector of FIG. 9 with the applicator and cartridge shown in section to reveal the interior thereof, with the medicament injector further including a retaining member having a catch and being shown in an extended position, and with the protrusion of the cartridge at the plunger-input end thereof engaging said catch;

FIG. 11 is a side elevation view of the medicament injector of FIG. 1, with the cartridge shown further inserted into the cartridge-accepting receptacle of the applicator, and with the valve actuator shown abutting an upper part of a ramp of the applicator;

FIG. 12 is a side perspective view of the medicament injector of FIG. 10 with the applicator and cartridge shown in section to reveal the interior thereof.

FIG. 15 is an enlarged side elevation view of the medicament injector of FIG. 14 shown in fragment and shown in section to reveal the interior thereof, with the valve actuator not being shown, with the valve body of the valve shown closer to the cartridge-accepting receptacle than in FIG. 14;

FIG. 16 is a side elevation view of the medicament injector of FIG. 1, with the cartridge shown fully inserted within the cartridge-accepting receptacle of the applicator;

FIG. 18 is a side elevation view of the medicament injector of FIG. 17 with the needle shown inserted into a patient, with the protective needle assembly shown in a retracted position, and with the plunger shown in a loaded position;

FIG. 19 is a side elevation view of the medicament injector of FIG. 18 with the plunger shown in an injecting-position so as to direct medicament from within the cartridge through the valve body, through the medicament-output end of the cartridge, through the conduit of the applicator, out of the needle and into the patient;

FIG. 21A is a front elevation view of a depressor of the medicament injector of FIG. 20;

FIG. 21B is a top, front, right side view of the depressor of FIG. 20;

FIG. 21C is a right side elevation view of the depressor of FIG. 20;

FIG. 21D is a sectional view taken along lines 21D-21D of the depressor of FIG. 21E;

FIG. 21E is a top plan view of the depressor of FIG. 20;

FIG. 22A is a front elevation view of a depressor housing of the medicament injector of FIG. 20;

FIG. 22B is a top, front, right side view of the depressor housing of FIG. 20;

FIG. 22C is a right side elevation view of the depressor housing of FIG. 20;

FIG. 22D is a top plan view of the depressor of FIG. 20;

FIG. 22E is a sectional view taken along lines 22E-22E of the depressor of FIG. 22F;

FIG. 22F is a rear elevation view of a depressor housing of the medicament injector of FIG. 20;

FIG. 22G is a top, rear, right side elevation view of the depressor housing of the medicament injector of FIG. 20;

FIG. 23 is a top, front, right side exploded view of the medicament injector of FIG. 20, with the depressor housing shown fully assembled and extending about the depressor, and the depressor housing shown in the process of coupling to a cartridge-accepting receptacle;

FIG. 24 is a top, front, right side exploded view of the medicament injector of FIG. 23, with the depressor housing shown coupled to the cartridge-accepting receptacle and the medicament injector further including an interchangeable cartridge shown in the process of being removed from the cartridge-accepting receptacle;

FIG. 25A is a front elevation view of the cartridge-accepting receptacle of FIG. 23;

FIG. 25B is a top, front, right side view of the cartridge-accepting receptacle of FIG. 23;

FIG. 25C is a sectional view taken along lines 25C-25C of the cartridge-accepting receptacle of FIG. 25D;

FIG. 25D is a right side elevation view of the cartridge-accepting receptacle of FIG. 23;

FIG. 25E is a top plan view of the cartridge-accepting receptacle of FIG. 23;

FIG. 27A is a left side, bottom, rear perspective view of the valve housing of the second valve of FIG. 26;

FIG. 27B is a right side elevation view of the valve housing of FIG. 27A;

FIG. 27C is a top plan view of the valve housing of FIG. 27A;

FIG. 27D is a left side elevation view of the valve housing of FIG. 27A;

FIG. 27E is a front, bottom, left side perspective view of the valve housing of FIG. 27A;

FIG. 27F is a front elevation view of the valve housing of FIG. 27A;

FIG. 28A is a bottom, right side, front perspective view of the valve member of the second valve of FIG. 26;

FIG. 28B is a top plan view of the valve member of FIG. 28A;

FIG. 28C is a right side elevation view of the valve member of FIG. 28A;

FIG. 28D is a bottom, right side, rear perspective view of the valve member of FIG. 28A;

FIG. 28E is a front elevation view of the valve member of FIG. 28A;

FIG. 30A is a top plan view of the body of the cartridge of FIG. 29;

FIG. 30B is a left side elevation view of the body of the cartridge of FIG. 30A;

FIG. 30C is a bottom, front, right side perspective view of the body of the cartridge of FIG. 30A;

FIG. 30D is a front elevation view of the body of the cartridge of FIG. 30A;

FIG. 30E is a rear elevation view of the body of the cartridge of FIG. 30A;

FIG. 31A is a rear elevation view of the retaining member of FIG. 20;

FIG. 31B is top plan view of the retaining member of FIG. 31A;

FIG. 31C is a left side elevation view of the retaining member of FIG. 31A;

FIG. 31D is a front, bottom, left side perspective view of the retaining member of FIG. 31A;

FIG. 31E is a front elevation view of the retaining member of FIG. 31D;

FIG. 33A is an enlarged fragmented view of the cartridge-accepting receptacle showing a linear set of teeth thereon, with the first valve and the second valve shown in closed positions, and each valve having circular gears, with the gears of the second valve in the process of engaging with the teeth of the cartridge to move the second valve from the closed position thereof to an open position thereof;

FIG. 33B is an exploded view of the medicament injector in the same position of FIG. 33A, with the cartridge in the processor of being inserted into the cartridge-accepting receptacle and sectional views of the valves being shown in their closed positions;

FIG. 34A is an enlarged fragmented view of the cartridge-accepting receptacle, with the teeth positioned between the first valve and the second valve, the second valve now in the closed position, the gears of the first valve in the process of engaging with the teeth the cartridge to move the first valve from the open position thereof to the closed position thereof;

FIG. 34B is an exploded view of the medicament injector in the same position of FIG. 34A, with the cartridge in the processor of being inserted into the cartridge-accepting receptacle and sectional views of the valves with the second valve show in the open position thereof and the first valve in the closed position thereof;

FIG. 36 is a side elevation view of the medicament injector of FIG. 35, with the depressor partially depressed towards the cartridge-accepting receptacle and shown in an injection mode, with the needle assembly piercing through into the barrel and being in fluid communication with the medicament;

FIG. 37 is a side elevation view of the medicament injector of FIG. 36, with the depressor fully depressed towards the cartridge-accepting receptacle and shown in said injection mode, with the needle assembly more fully extending into the barrel and being in fluid communication with the medicament.

DESCRIPTION OF THE PREFERRED EMBODIMENTS

Figure 6:
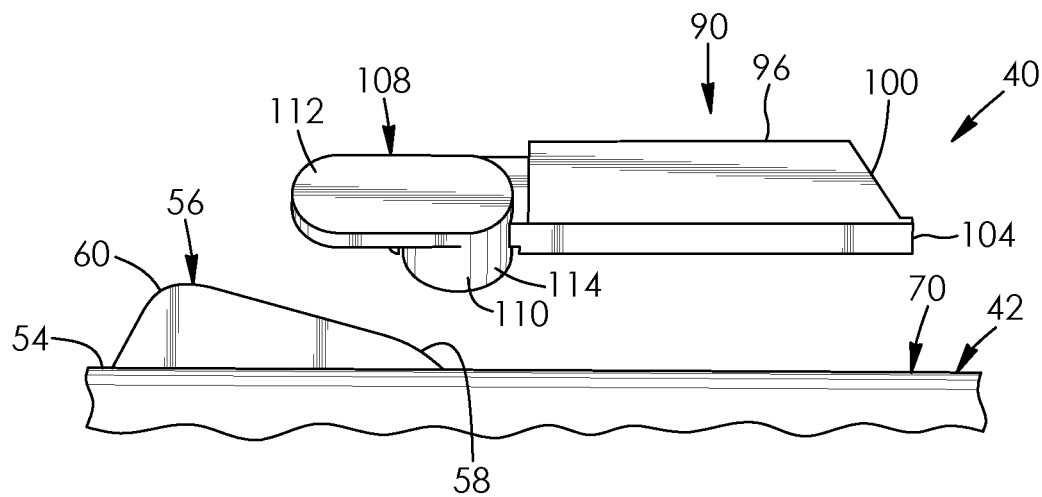
FIG. 6 is a bottom, side perspective view of the cartridge of FIG. 1, together with the cartridge-accepting receptacle of the applicator of FIG. 1 being shown in fragment.
Figure 7:
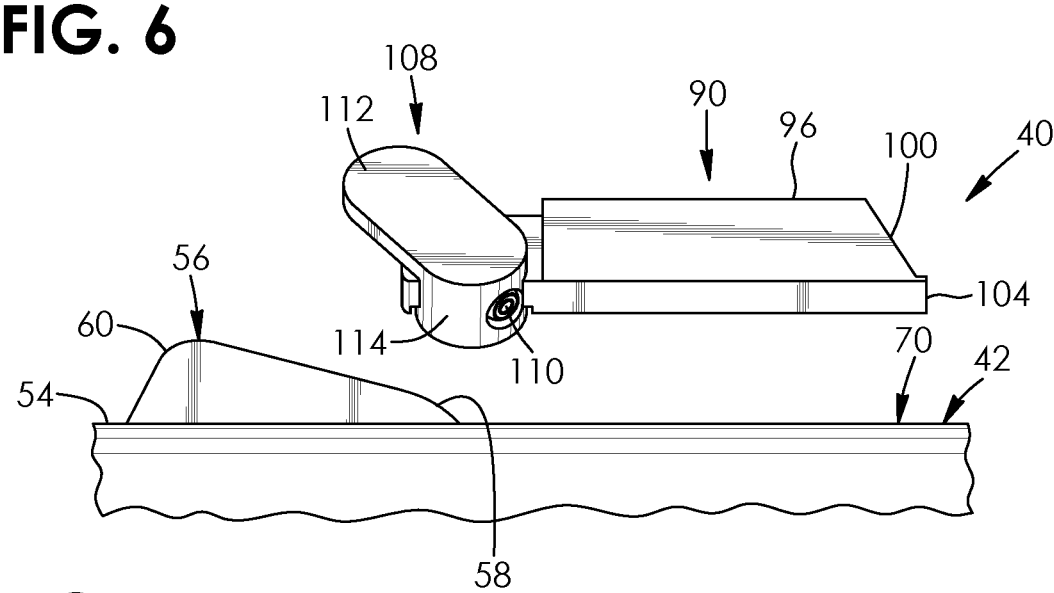
FIG. 7 is a bottom, side perspective view of the cartridge of FIG. 1, together with the cartridge-accepting receptacle of the applicator of FIG. 1 being shown in fragment, with the valve actuator of the cartridge shown partially actuated.
Figure 8:
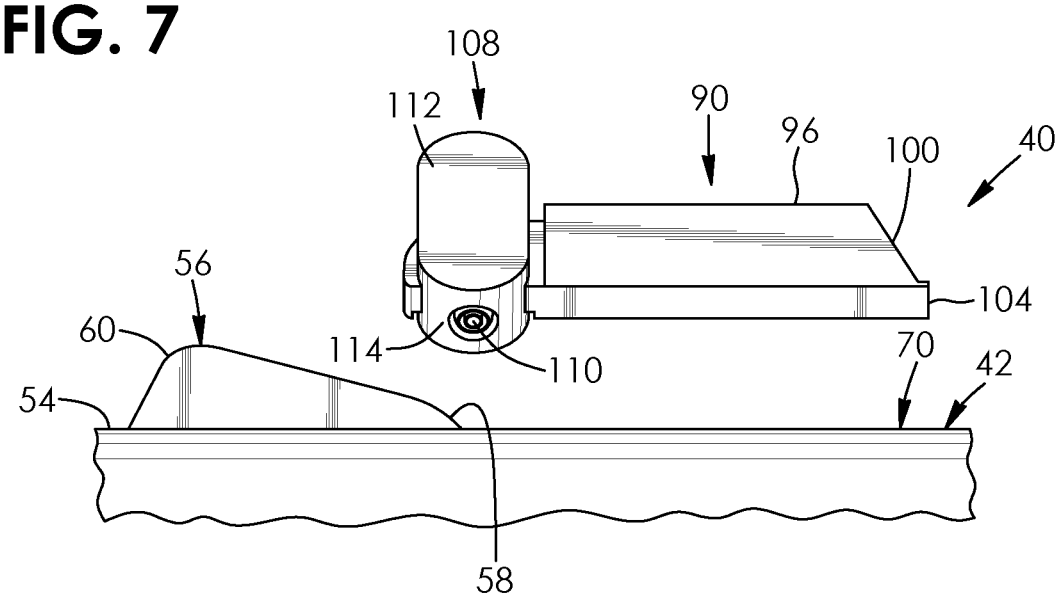
FIG. 8 is a bottom, side perspective view of the cartridge of FIG. 1, together with the cartridge-accepting receptacle of the applicator of FIG. 1 being shown in fragment, with the valve actuator of the cartridge shown fully actuated.

Referring to the drawings and first to FIG. 1, there is shown a medicament injector 40.

The medicament injector includes a cartridge applicator 42 which is generally a cylindrical body that is hollow at least in part and which extends along a longitudinal axis 43. The applicator includes a depressor, in this example plunger 44 adjacent to a first end 46 thereof. As seen in FIG. 12, the plunger has a first or outer end, in this example a gripping end 39 and a second or inner end, in this example a distal end 41. The plunger 44 is moveable from a loaded position shown in FIG. 1 to an injecting-position shown in FIG. 19. As seen in FIG. 2, the applicator 42 includes a depressor bore, in this example a plunger bore 45 that, in this embodiment, is offset from axis 43 and which extends parallel with the axis 43 in this example. The plunger bore is extends to end 46 of the applicator and is shaped to slidably receive plunger 44 therewithin.

The applicator 42 includes a needle protection assembly 48 adjacent to a second end 50 thereof. The needle protection assembly selectively extends about needle 52 seen in FIGS. 18 and 19. The parts and functioning of an example of a suitable needle protection assembly in this regard is described in U.S. Provisional Patent Application No. 62/518,689, the disclosure of which is incorporated herein by reference and priority to which is claimed.

Referring to FIG. 2, the applicator 42 includes a conduit 53 having a first end (not shown) configured to couple with the needle 52 of FIG. 18. As seen in FIG. 15, the conduit has a second end 55. The conduit comprises one of at least one male member and at least one female member, in this example comprising a plurality of male members, in this case circumferentially spaced-apart detents 57 at said end 55.

Referring back to FIG. 1, the applicator 42 includes a side wall, in this example an annular side wall 54 and a protuberance, in this example a ramp 56 which is coupled to and extends outwards from said side wall. The ramp is generally triangular in side profile in this example and is between the ends 46 and 50 of the applicator. The ramp 56 has a thin end 58 adjacent to the side wall 54 of the applicator 42 and a larger or thicker end 60 radially spaced-apart further from the side wall of the applicator. As seen in FIG. 4, the ramp 56 has a recessed track 62 thereon comprising a pair of spaced-apart, recessed shoulders 64 and 66 between which extends a further recessed, centrally-positioned channel 68.

As seen in FIG. 10, the applicator 42 includes a cartridge-accepting receptacle 70 between the ends 46 and 50 thereof. As seen in FIG. 19, the cartridge-accepting receptacle is coupled to the needle 52. Referring back to FIG. 10, the cartridge-accepting receptacle has an opening 72 which extends through annular side wall 54 of the applicator and which is generally rectangular in shape in this example. The cartridge-accepting receptacle 70 is between the ramp 56 and the plunger bore 45 in this example, and is in fluid communication with the plunger bore. The cartridge-accepting receptacle extends in a direction parallel with the longitudinal axis 43 of the applicator 42 in this example.

Referring to FIGS. 3 and 15, the cartridge-accepting receptacle 70 has an enlarged portion 73 adjacent to the ramp 56 in this example. The enlarged portion is generally annular in shape in this case.

Still referring to FIG. 10, the applicator 42 includes an inner track 74 which is in communication with the cartridge-accepting receptacle 70 and which extends between the ramp 56 and end 46 thereof. The track is generally a rectangular prism in shape in this example and extends parallel with longitudinal axis 43 of the applicator 42.

As seen in FIG. 12, the medicament injector 40 includes a retaining member 76. The retaining member is shaped to slidably engage with inner track 74 of the applicator 42 via an inverse u-shaped bottom 78 in this example. The retaining member is elongate and extends parallel with the longitudinal axis 43 of the applicator 42 in this example. The retaining member 76 includes one of a catch and protrusion, in this example a catch 80 coupled to and extending upwards from a top 82 thereof.

As seen in FIG. 2, the retaining member 76 is biased towards a closed or extended position, in which the catch extends within the cartridge-accepting receptacle 70, via a resilient member, in this example a spring 84. The spring extends along the inner track 74 in this example, with a first end 86 which abuts the applicator 42 adjacent to the distal end 41 of the plunger 44 in this example. The spring 84 has a second end 88 which abuts the retaining member 76.

Figure 17:
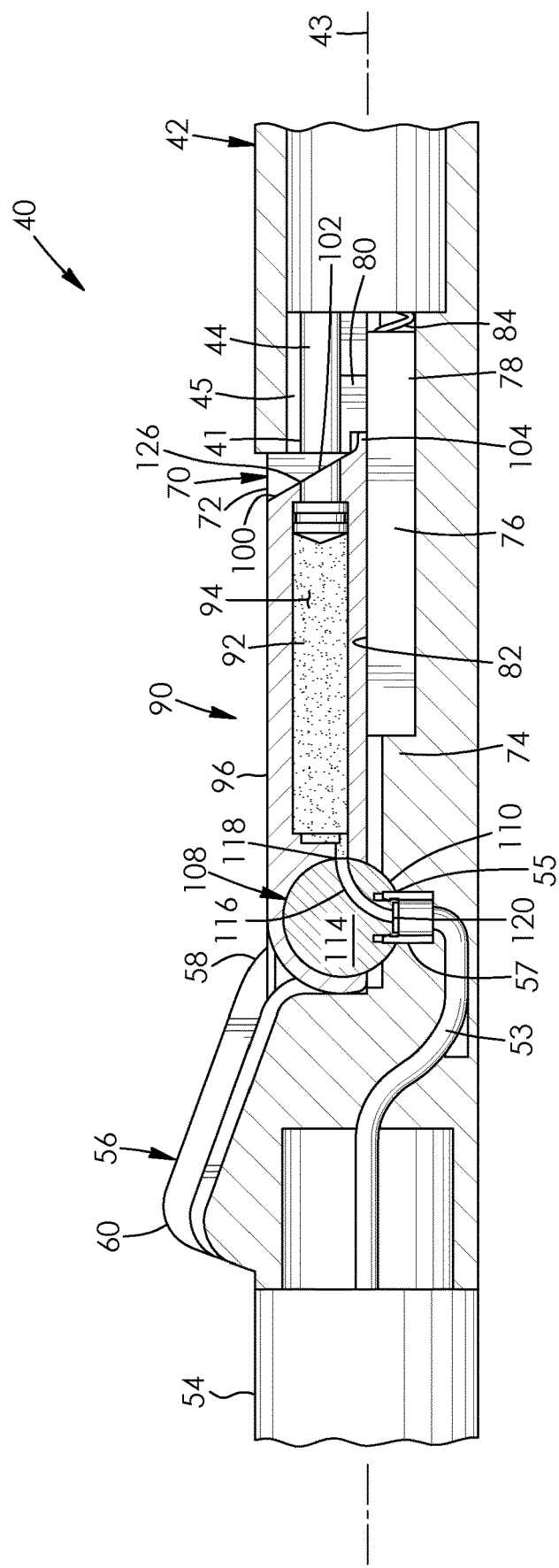
FIG. 17 is a side elevation view of the medicament injector of FIG. 16 with the applicator and cartridge shown in section to reveal the interior thereof, with the retaining member shown in a retracted position and shown retaining the cartridge in place, with the plunger-input end of the cartridge in communication with the plunger of the applicator, with the valve in the open position so as to enable the interior of the cartridge to be in communication with a needle conduit of the applicator, and with detents of the applicator shown coupling to complementary recesses of the valve body of the cartridge to further retain the cartridge in place.

The retaining member is moveable along inner track 74 from the extended position seen in FIG. 2, to an open or retracted position seen in FIG. 17. The catch 80 is free of the cartridge-accepting receptacle 70 when the retaining member is in its retracted position.

Referring to FIG. 1, the medicament injector 40 includes a plurality of interchangeable cartridges, as shown by interchangeable cartridge 90. Referring to FIG. 2, the cartridge receives a medicament 92 within an interior 94 thereof. The cartridge includes an elongate, hollow body 96 with a bore 98 within which the medicament is contained and received. As seen in FIG. 17, the elongate body extends parallel with the longitudinal axis 43 of the applicator 42 when the cartridge 90 is fully inserted into the cartridge-accepting receptacle 70.

Referring to FIG. 1, the cartridge has a first and in this example plunger-input end 100 that is angled in this example. As seen in FIG. 4, the plunger-input end of the cartridge is in the shape of an isosceles trapezoid in this example and has an opening 102. Referring to FIG. 19, bore 98 is shaped to slidably receive the plunger 44 via the opening 102 of the plunger-input end 100 of the cartridge 90. Referring back to FIG. 1, the cartridge includes one of a catch or a protrusion, in this example a protrusion 104. The protrusion is generally a rectangular prism in shape in this example.

Figure 13:
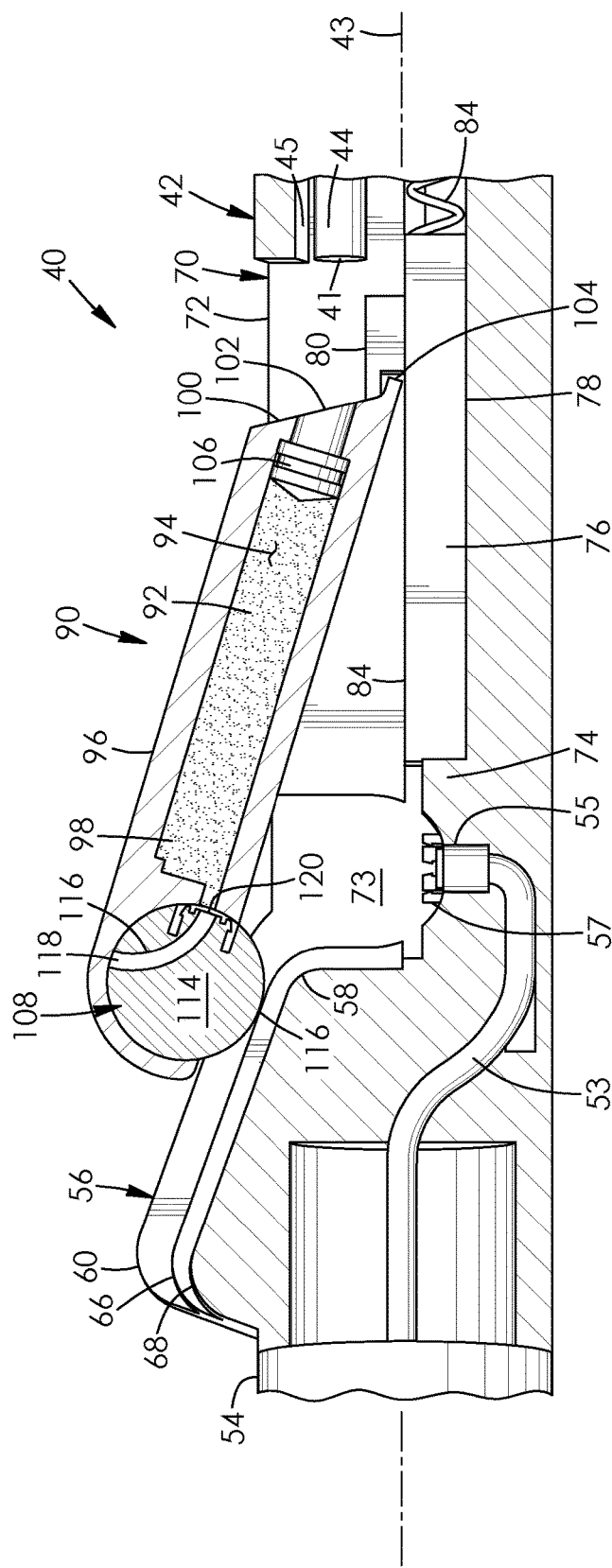
FIG. 13 is an enlarged side elevation view of the medicament injector of FIG. 1 shown in fragment and shown in section to reveal the interior thereof, with the valve actuator not being shown, with a valve body of the valve shown inserted yet further into the cartridge-accepting receptacle than in FIG. 12, and with the valve shown in its closed position.

As seen in FIG. 13, the cartridge 90 includes a piston member, in this example a piston 106 sealably disposed within the bore 98 thereof. The piston is longitudinally moveable along the bore and is positioned between the opening 102 of the plunger-input end 100 of the cartridge and the interior 94 of the cartridge.

As seen in FIG. 1, the cartridge 90 includes a barrier member, in this example valve 108 at a medicament-output end 110 thereof. The piston 106 is positioned between ends 100 and 110 of the cartridge. The valve 108 is pivotably coupled and thus rotatable relative to the body 96 of the cartridge 90.

The valve includes a valve actuator, in this example an elongate lever 112 that pivotally couples to the body of the cartridge. The lever is obround in side view in this example. As seen in FIG. 15, the valve 108 includes a valve body 114 that is generally cylindrical in side view in this example. The valve includes a conduit 116 which is arcuate-shaped in this example and which extends through the valve body. The conduit has an inlet 118 and an outlet 120. The valve includes a member shaped to mate with the detents, in this example via recesses 122 of the valve body 114 which are adjacent to outlet 120 of the conduit 116.

Referring to FIG. 1, the valve 108 has a closed position in which fluid communication between the hollow body 96 and the medicament-output end 110 of the cartridge 90 is inhibited. This is a pre-injection mode of the cartridge and the valve thus inhibits access to the medicament 92 seen in FIG. 1 when the cartridge 90 is in the pre-injection mode. As seen in FIGS. 13 and 15, fluid communication between the inlet 118 of conduit 116 and interior 94 of the cartridge is inhibited when the valve is in its closed position. As seen in FIG. 1, the valve 108 extends substantially parallel to the body 96 of the cartridge 90 when the valve is in its fully closed position in this example.

Referring to FIG. 10, in order to insert the cartridge 90 into the cartridge-accepting receptacle 70 of the applicator 42, protrusion 104 of the cartridge 90 is first engaged with the catch 80 of the retaining member 76.

As seen in FIG. 11, the lever 112 next abuts against and is slid along the recessed track 62 of the ramp 56 of the applicator. The cartridge 90 is next moved to the right, from the perspective of FIG. 11 as shown by arrow of numeral 124, so as to cause the valve member to slide down the ramp towards the cartridge-accepting receptacle 70. At the same time, this movement of the cartridge to the right causes the retaining member 76 to move from its extended position towards its retracted position seen in FIG. 19, thereby freeing room for the cartridge 90 to be inserted into the cartridge-accepting receptacle 70.

Figure 14:
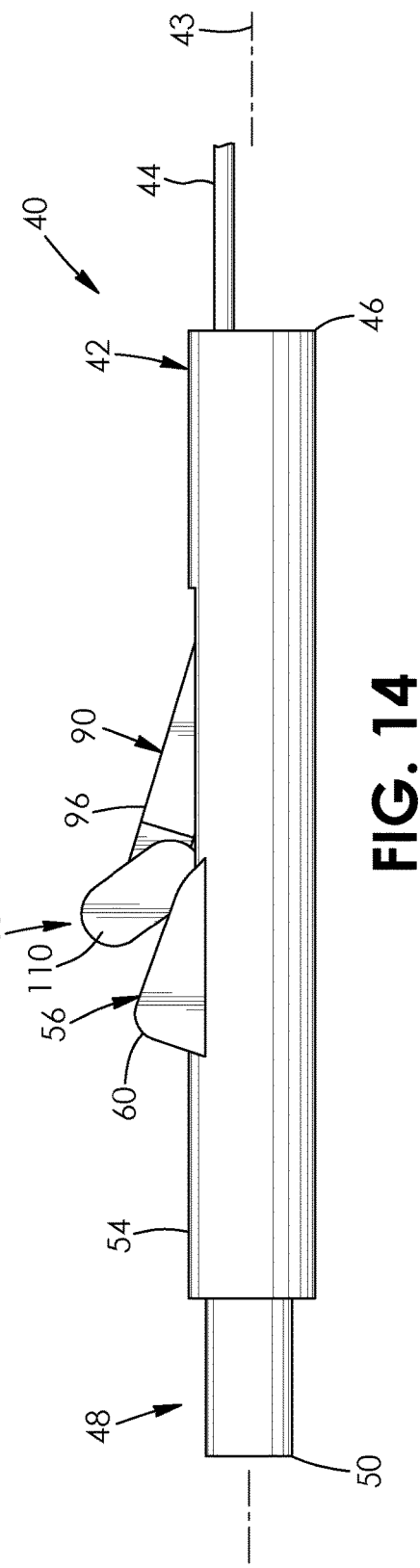
FIG. 14 is a side perspective view of the medicament injector of FIG. 1, with the cartridge shown still further inserted into the cartridge-accepting receptacle compared to FIG. 13, with the valve actuator beginning to enter the cartridge-accepting receptacle and with the ramp of the applicator actuating the valve actuator so as to cause the valve to move from the closed position towards the open position thereof.

Referring to FIGS. 1, 14, and 16, the ramp 56 functions to move the lever 112 from its closed position seen in FIG. 1, to an open position seen in FIG. 16. As seen in FIG. 17, when the valve is in its open position, inlet 118 of conduit 116 is in communication with the interior 94 of the cartridge 90 and outlet 120 of the conduit is in communication with the conduit 53 of the applicator 42. Fluid communication between the medicament 92 and the medicament-output end 110 of the cartridge is promoted thereby. The lever 112 in its fully open position also enables detents 57 of the applicator to align with recesses of the valve body 114 and couple to the valve body thereby. Thus, insertion of the cartridge 90 into the applicator 42 causes the valve 108 to rotate from its closed position seen in FIG. 1 to its open position seen in FIG. 16, and enable the medicament 92 seen in FIG. 17 to be accessible by the applicator 42. Insertion of the cartridge into the cartridge-accepting receptacle causes the cartridge to move from the pre-injection mode seen in FIG. 1 to an injection mode in which the medicament is accessible via the needle 52 seen in FIG. 19.

Insertion of the cartridge into the cartridge-accepting receptacle thus causes: the plunger-input end 100 of the cartridge 90 to be in fluid communication with the plunger, with said end abutting a corresponding tapered portion 126 of the applicator 42 as seen in FIG. 17. Insertion of the cartridge into the cartridge-accepting receptacle further causes the interior 94 of the cartridge to be in fluid communication with the medicament-output end 110 of the cartridge. Insertion of the cartridge into the cartridge-accepting receptacle also causes the medicament-output end of the cartridge to be in fluid communication with the conduit 53 of the applicator 42.

Referring to FIG. 18, spring 84 biases the retaining member 76 to abut the cartridge 90 so fully inserted so as to inhibit removal of the cartridge from the cartridge-accepting receptacle. The retaining member is thus shaped to also inhibit removal of the cartridge so fully inserted within the cartridge-accepting receptacle 70.

Referring to FIG. 16, removing the cartridge 90 from the cartridge-accepting receptacle 70 by, for example, pushing rearwards on the lever 112 as seen by arrow of numeral 91, causes the valve 108 to move from its open position to its closed position seen in FIG. 1 once more.

FIGS. 20 to 37 shows a medicament injector 40.1 according to another embodiment. Like parts have like numbers and function as the embodiment shown in FIGS. 1 to 19 with the addition of "0.1". Medicament injector 40.1 is similar to medicament injector 40 as shown in FIGS. 1 to 19 with the following exceptions.

Figure 20:
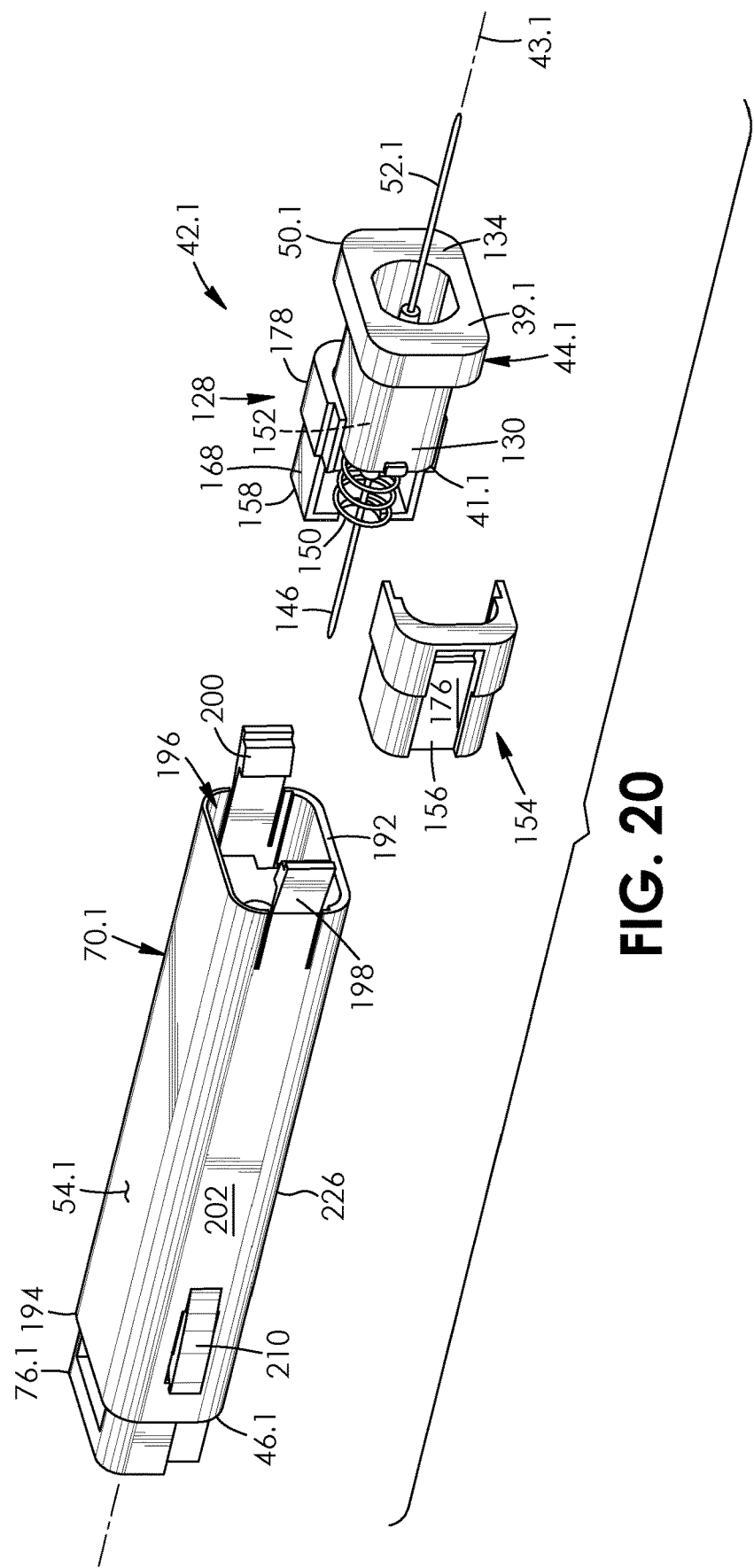
FIG. 20 is a top, front, right side exploded view of a medicament injector according to a second embodiment.

As seen in FIG. 20, applicator 42.1 includes a needle assembly 128. The needle assembly may be referred to in part as a patient-facing portion of the applicator adapted for variable injection mechanisms including at least one of IM (intramuscular) needle delivery, IV (intravenous) fluid connection delivery with a standard IV tubing and Luer Lock™ mechanism, and IN (intranasal) medicament atomizer delivery. The needle assembly 128 includes a depressor 44.1 which extends from the end 50.1 of the applicator towards 46.1 of the applicator. The depressor may be referred to as a plunger mechanism or a pneumatic delivery system. As seen in FIG. 21D, the depressor has a base 130 which extends from end 41.1 thereof towards end 39.1 thereof. A passageway 132 extends through the base parallel with axis 43.1 in this example. The depressor 44.1 includes an enlarged flange 134 at end 39.1 thereof. The flange is a rectangular prism in outer shape in this example and is shaped to abut a patient's skin (not shown). The depressor includes a sleeve portion 136 which extends between and couples together the base 130 thereof and the flange thereof. The sleeve portion is rectangular in cross-section in this example, though this is not strictly required. The flange 134 extends radially outwards relative to the sleeve portion 136 and base 130. As seen in FIG. 21E, the depressor 44.1 includes a guide member, in this example a pair of spaced-apart protrusions 138 and 140 coupled to and extending outwards from the base of the depressor adjacent to end 41.1 of the depressor.

As seen in FIG. 21D, the depressor includes a pair of mounts, in this example a pair of opposed male Luer-Lock™ fittings 142 and 144 positioned on either side of passageway 132. Luer-lock fittings, including their various parts and functions, are known per se by one skilled in the art and thus will not be described in further detail. Luer-Lock™ fittings 142 and 144 is shaped to selectively coupled with a first or outer needle 52.1 seen in FIG. 20 via a female Luer-lock™ fitting (not shown) and a second or inner needle 146 via a female Luer-lock™ fitting (not shown) in a conventional manner. The needles are in fluid communication with each other via passageway 132 seen in FIG. 21D. As seen in FIG. 20, the inner and outer needles thus couples to the depressor, with the outer needle 52.1 extending outwards from end 39.1 of the depressor and the inner needle 146 extending outwards from end 41.1 of the depressor.

Still referring to FIG. 20, sleeve portion 136 encloses outer needle 52.1 at least in part. Referring back to FIG. 21D, the depressor 44.1 further includes an annular recess 148 adjacent to Luer-lock fitting 144. As seen in FIG. 20, the applicator includes a first resilient member, in this example a coil spring 150 with a first end thereof 152 which fits within recess 148 seen in FIG. 21D.

As seen in FIG. 20, the applicator 42.1 includes a depressor housing 154 comprises of two parts 156 and 158. The parts couple together via complementary snap fittings 160 and 162 seen in FIG. 22A. As seen in FIG. 22E, the depressor housing has a closed or inner end 164 and an open, outer end 166. The depressor housing 154 has a base 168 which extends from end 164 thereof towards end 166 thereof. As seen in FIG. 22E, a passageway 170 extends through the base parallel with axis 43.1 in this example. The depressor housing 154 includes an enlarged flange 172 at end 166 thereof. The flange is a rectangular prism in outer shape in this example. The depressor housing includes a sleeve portion 174 which extends between and couples together the base 168 thereof and the flange thereof. The sleeve portion is generally rectangular in cross-section in this example, though this is not strictly required. The flange 172 extends radially outwards relative to the sleeve portion 174 and base 168.

As seen in FIG. 22B, the depressor housing 154 has a bore 45.1 and the sleeve portion 174 includes a pair of spaced-apart walls 176 and 178 with inner surfaces 177 and 179 which face each other and which are in fluid communication with the bore. As seen in FIG. 22E, the depressor housing includes a pair of inner guides, in this example guide channels 180 and 182. The bore 45.1 is shaped to receive the base 130 and sleeve portion 136 of the depressor 44.1 seen in FIG. 21E, with the protrusions 138 and 140 of the depressor being received within and slidable along the guide channels 180 seen in FIG. 22B. Spring 150 seen in FIG. 20 is positioned between base 130 of depressor 44.1 and base 168 of the depressor so as to bias the depressor axially outwards relative to the depressor housing. As seen in FIG. 24, the needle assembly 128 is thus coupled to and resiliently biased outwards from cartridge-accepting receptacle 70.1.

Figure 35:
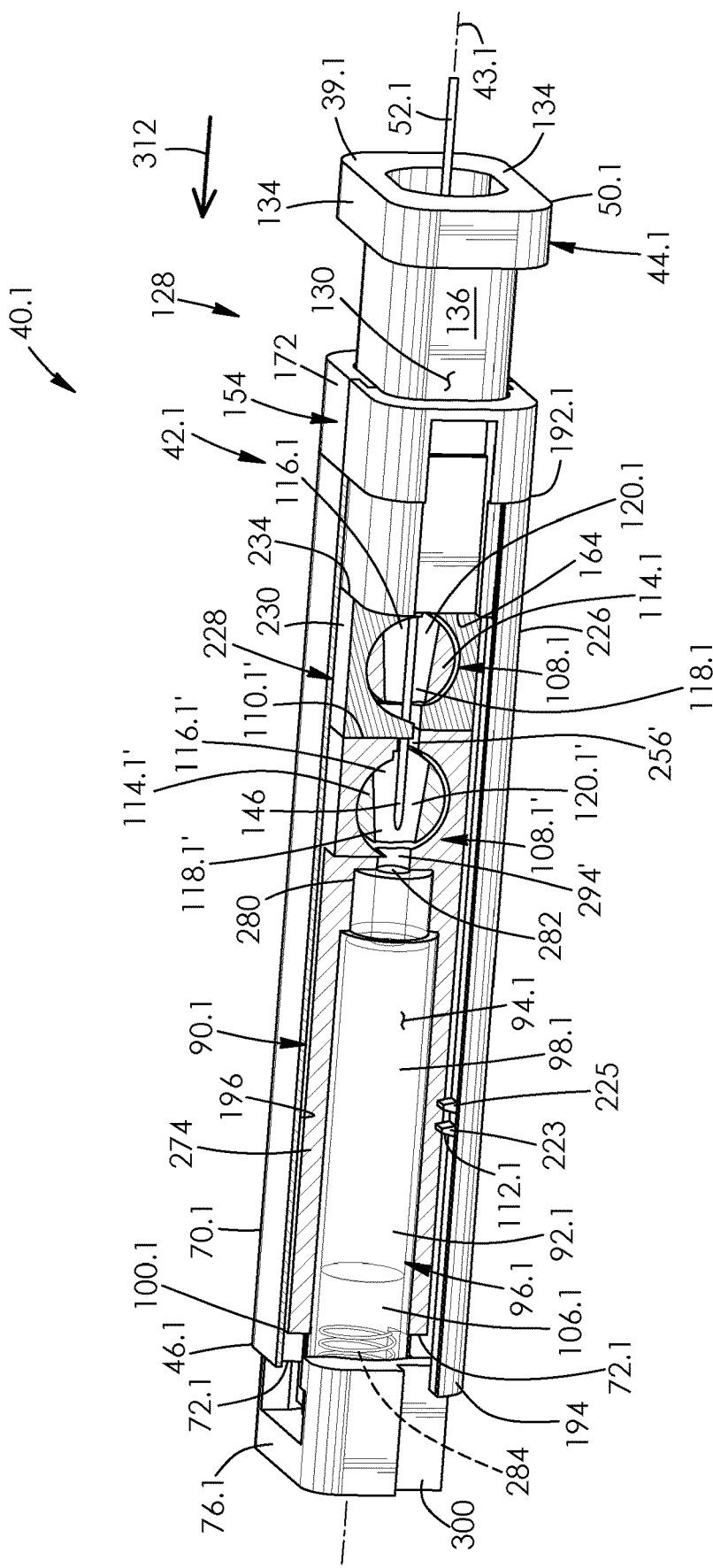
FIG. 35 is a side elevation view of the medicament injector of FIG. 20, with the cartridge fully inserted into the cartridge-accepting receptacle, the medicament injector including a needle assembly coupled to the depressor, and the depressor being shown in pre-injection mode with the needle assembly spaced forward of the barrel containing medicament.

The depressor has a pre-injection position seen in FIG. 35 in which flange 134 of the depressor is space-apart from flange 172 of the depressor housing 154. The depressor 44.1 is linearly moveable via the protrusions 138 and 140 seen in FIG. 21E and guide channels 180 and 182 seen in FIG. 22E, from the pre-injection position of FIG. 35 to an injection position seen in FIG. 37. As seen in FIGS. 37, flanges 134 and 172 abut each other in the injection position.

Referring back to FIG. 22E, the depressor housing 154 includes a pair of spaced-apart outer female locking members, in this example recessed portions 184 and 186 which extend inwards from outer surfaces 188 and 190 of walls.

As seen in FIG. 20, the applicator 42.1 includes a cartridge-accepting receptacle 70.1 that is tubular in this example and generally rectangular in cross-section in this case. The cartridge-accepting receptacle has a first open end 192 and a second open end 194, which coincides with end 46.1 of the applicator. The cartridge-accepting receptacle 70.1 includes a bore 196 which extends from the first to the second end thereof.

As seen with reference to FIGS. 23 and 24, bore 196 is shaped to receive base 168 and sleeve portion 174 of depressor housing 154 such that end 192 of the cartridge-accepting receptacle 70.1 abuts flange 134 of the depressor housing seen in FIG. 21D. Referring to FIG. 25B, the cartridge-accepting receptacle selectively couples to the depressor housing, in this example via a first pair of spaced-apart, resilient catch members 198 and 200 which couple to and extend outwards from opposed first and second walls 202 and 204 of the cartridge-accepting receptacle. As seen in FIG. 25C, the catch members include protuberances 206 and 208 shaped to fit within recessed portions 184 of depressor housing 154 as seen with reference to FIGS. 23 and 24.

As seen in FIG. 25A, the cartridge-accepting receptacle 70.1 includes a pair of guides, in this example spaced-apart longitudinally-extending protrusions 209 and 211. Referring to FIG. 25C, the cartridge-accepting receptacle includes of a third wall 226 to which the protrusions couple and along which the protrusions extend. The third wall is coupled to and extends between walls 202 and 204. The protrusions 209 and 211 extend from near end 192 of the cartridge-accepting receptacle to end 194 of the cartridge-accepting receptacle. The protrusions 209 and 211 are rectangular prisms in shape in this example.

As seen in FIG. 25C, the cartridge-accepting receptacle 70.1 includes a second pair of spaced-apart, resilient catch members 210 and 212 spaced from and near end 194 thereof. The catch members includes protuberances 214 and 216 which extend in part within bore 196 and interior 215 of the cartridge-accepting receptacle.

As seen in FIG. 25C, the applicator 42.1 includes a valve actuator, in this example linear gears, in this example in the form of a pair of spaced-apart rows 218 and 220 of linear gears 112.1 and 222, each comprising teeth 223 and 225, and teeth 227 and 229. Linear gears 112.1 are adjacent to wall 202 of the cartridge-accepting receptacle and linear gears 222 are adjacent to wall 204 of the cartridge-accepting receptacle. The linear gears are interposed between ends 192 and 194 of the cartridge-accepting receptacle 70.1 and in this example are positioned adjacent to catch members 210 and 212. Referring to FIG. 25C, the linear gears 112.1 and 222 are in fluid communication with bore 196 and couple to and extend upwards from respective longitudinally-extending protrusions 209 and 211 of the cartridge-accepting receptacle in this example.

Figure 26:
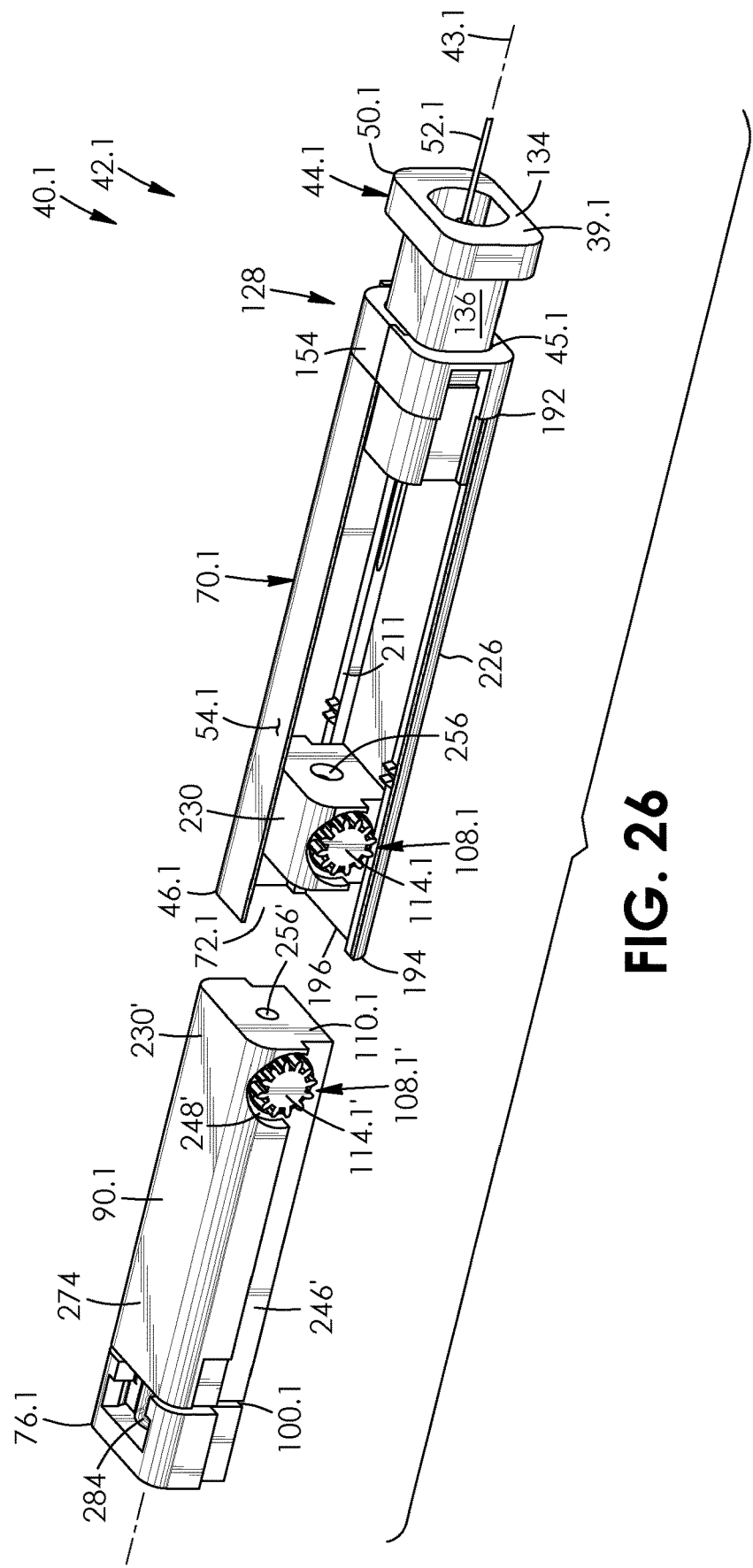
FIG. 26 is a top, front, right side exploded view of the medicament injector of FIG. 23, with the cartridge shown fully removed from the cartridge-accepting receptacle to reveal a first valve thereof and with the cartridge-accepting receptacle shown partially in fragment to reveal interior contents thereof including a second valve thereof, the second valve including a valve housing and a valve member disposed within the valve housing.

As seen in FIG. 26, the medicament injector 40.1 includes a first barrier member, in this example a valve 108.1. The valve includes a valve housing 230 best seen in FIGS. 27A to 27F. The valve housing is generally block-like and a rectangular prism in shape in this example. As seen in FIG. 27A, the valve housing includes a first or rear end 232, a second or front end 234, a top 236, and a bottom 238 and a pair of sides 240 and 242 which extend between the top and bottom thereof and ends thereof. The valve housing 230 has a pair of spaced-apart lower recessed regions 244 and 246 along sides thereof. As seen in FIG. 33A, the valve housing 230 is shaped to slidably extend within bore 196 of the cartridge-accepting receptacle 70.1 with protrusions 209 and 211 extending within the recessed regions 244 and 246 of the valve housing.

Referring back to FIG. 27A, the valve 108.1 includes a bore 248 which extends through the sides 240 and 242 of the valve housing and which is positioned between the rear end 232 and front end 234 of the valve housing. As seen in FIG. 33A, the bore extends along a lateral axis 249 which is perpendicular to axis 43.1 of the medicament injector 40.1. As seen in FIG. 27E, the valve has at least one, in this example a pair of spaced-apart tracks, in this case recessed channels 250 and 252 positioned between the sides 240 and 242, top 236 and bottom 238, and ends 232 and 234 of the valve housing. The channels are arc-shaped in side profile in this example and in fluid communication with the bore 248. The channels 250 and 252 are rectangular in lateral cross-section in this example.

As seen in FIG. 27A, the valve housing 230 has a first or rear aperture 254 which extends through rear end 232 thereof and which is in fluid communication with bore 248. As seen in FIG. 27E, the valve housing has a second or front aperture 256 which extends through the front end 234 thereof and which is also in fluid communication with the bore. Each of the apertures is circular in this example, with front aperture 256 being larger than rear aperture 254 in this example.

As seen in FIGS. 28A to 28E, the valve 108.1 includes a valve body 114.1 which is generally cylindrical in shape in this example. The body includes a pair of circular gears 258 and 260 at spaced-apart ends 262 and 264 thereof. As seen in FIG. 28E, the valve body includes a conduit, in this example a tapered passageway 116.1 that is tapered in this example from outlet 120.1 towards inlet 118.1. The passageway extends from the top 266 to the bottom 268 of the valve body and is positioned between ends 262 and 262 of the valve body. As seen with reference to FIGS. 28B and 28E, the valve body 114.1 includes at least one, and in this example a pair of spaced-apart guides, in this example protrusions 270 and 272 coupled to and extending upwards from the top 266 of the valve body relative to the FIGS. 28B and 28E. Each of the protrusions is generally a rectangular prism in shape in this example. The protrusions are positioned between gears 258 and 260, and adjacent to outlet 120.1 of passageway 116.1 in this example.

Referring to FIGS. 27A and 28A, the valve body 114.1 is shaped to fit within bore 248 of valve housing 230, with protrusions 270 and 272 shaped to fit within and be moveable relative to recessed channels 250 and 252 seen in FIG. 27E. The valve 108.1 has a closed position seen in FIGS. 28A, 33A and 33B in which passageway 116.1 seen in FIG. 28A is not in fluid communication with apertures 254 and 254 of the valve housing seen in FIG. 27F.

Referring to FIG. 33A, insertion of valve 108.1 into the cartridge-accepting receptacle 70.1 causes gears 258 and 112.1 to engage with each other, such that the valve 108.1 moves from the closed position seen in in FIG. 33B to an open position seen in FIG. 34B. Passageway 116.1 is in fluid communication with apertures 254 and 254 of the valve housing seen in FIG. 27F when the valve 108.1 in the open position.

As seen in FIG. 26, the medicament injector 40.1 includes an interchangeable cartridge 90.1. As seen in FIG. 35, valve 108.1 is interposed between the needle assembly 128 and the cartridge. Referring back to FIG. 26, the cartridge 90.1 includes a barrier member, in this example a valve 108'. Like parts have like numbers as the valve 108.1 seen in FIGS. 27A to 27F with the addition of Referring to FIGS. 30A and 30C, the valve includes a valve housing 230' adjacent to end 110.1' thereof. The valve housing has a bore 248' which extends between sides 240' and 242' thereof. The valve housing 230' includes a pair of spaced-apart recessed channels 250' and 252' in communication with bore 248' and also adjacent to end 110.1 thereof. As seen in FIG. 26, the valve 108.1' includes a valve body 114.1' shaped to fit within bore 248' and engage with the valve housing in a substantially similar manner as valve body 114.1 with valve housing 230. As seen in FIG. 30A, the cartridge 90.1 includes an aperture 256' which is in fluid communication with bore 248'.

Referring to FIG. 30C, the cartridge 90.1 includes a cartridge housing 274 of which valve housing 230' is integrally connected and formed therewith. The cartridge housing has a pair of spaced-apart lower recessed regions 244' and 246' along sides 240' and 242' thereof. As seen in FIG. 33A, the valve housing 230 is shaped to slidably extend within bore 196 of the cartridge-accepting receptacle 70.1 with protrusions 209 and 211 extending within the recessed regions 244' and 246' of the cartridge housing.

Referring to FIGS. 25C and 30C, cartridge 90.1 is shaped to selectively fit within and couple to the cartridge-accepting receptacle via a locking mechanism, in this example a snap-fit system. The snap-fit system comprises catch members 210 and 212 seen in FIG. 25C which couple with corresponding outer female locking members, in this example recessed portions 273 and 275, seen in FIG. 30A. The recessed portions extend inwards from sides 240' and 242' of the cartridge housing 274 and are positioned to extend end 100.1 towards end 110.1 of the cartridge 90.1.

Figure 29:
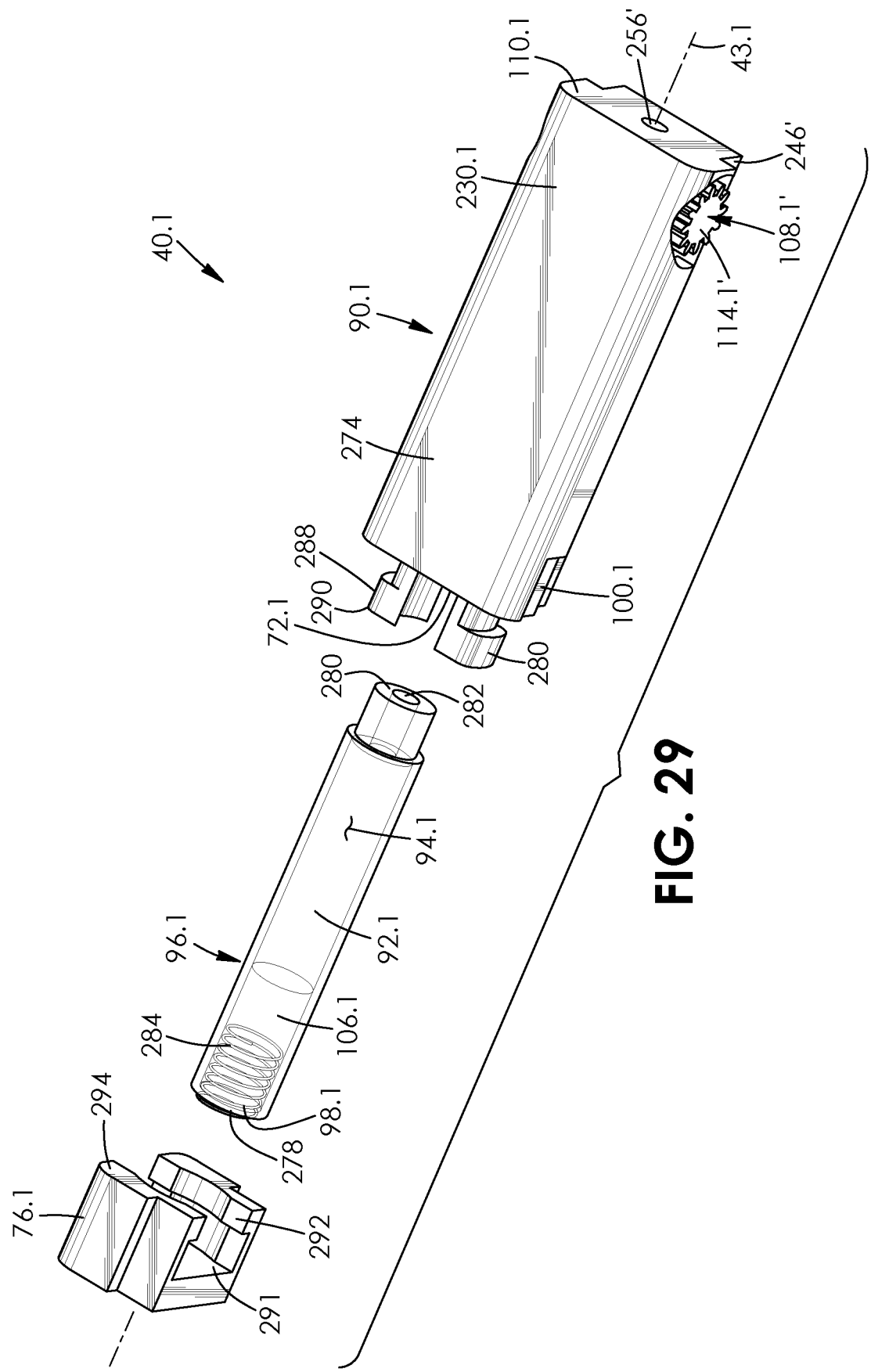
FIG. 29 is a top, right side, front exploded view of the cartridge of FIG. 26, the cartridge including a body, a barrel containing medicament, and a retaining member shown in an unlocked position.

Referring to FIG. 30A, the cartridge housing 274 extends between ends 110.1 and 100.1 thereof. The cartridge 90.1 includes a central bore 276 which extends from open end 100.1 thereof towards end 110.1 thereof. Bore 276 extends along axis 43, extends perpendicular to bore 248' in this example and is in fluid communication with bore 248' via aperture 254'. As seen in FIG. 29, the cartridge 90.1 includes a body, in this example a barrel 96.1 within which medicament 92.1 is contained or received. As seen in FIG. 33B, bore 276 is shaped to receive the barrel.

Referring back to FIG. 29, the barrel 96.1 has a bore 98.1 with an open first end 278 and a second end 280 with a sealed opening 282. The barrel includes a piston 106.1 between the ends thereof. The medicament 92.1 is positioned within the bore 98.1 between the piston and sealed opening 282. The cartridge 90.1 includes a resilient member, in this example a coil spring 284 positioned within the bore and extending from end 278 towards end 280. The coil spring is configured to bias the piston 106.1 and thus the medicament 92.1 towards the sealed opening 282. The spring 284 thus causes the medicament to be enclosed within the barrel 96.1 under pressure. The barrel 96.1, spring 284 and piston 106.1 may thus be referred to as a spring-loaded delivery system.

Figure 32A:
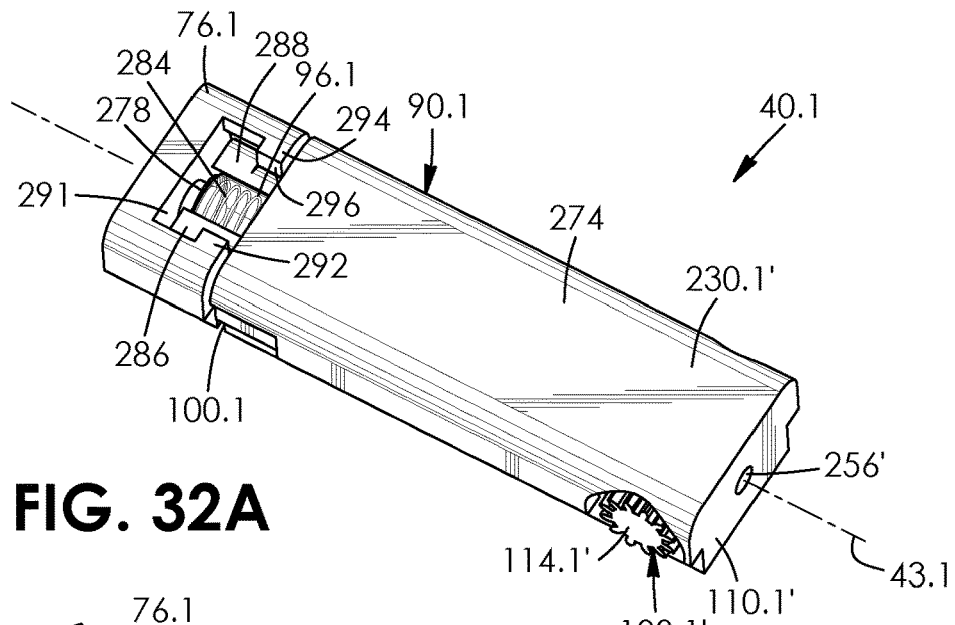
FIG. 32A is a front, top, right side perspective view of the cartridge of FIG. 29, with the retaining member shown in a locked position.
Figure 32B:
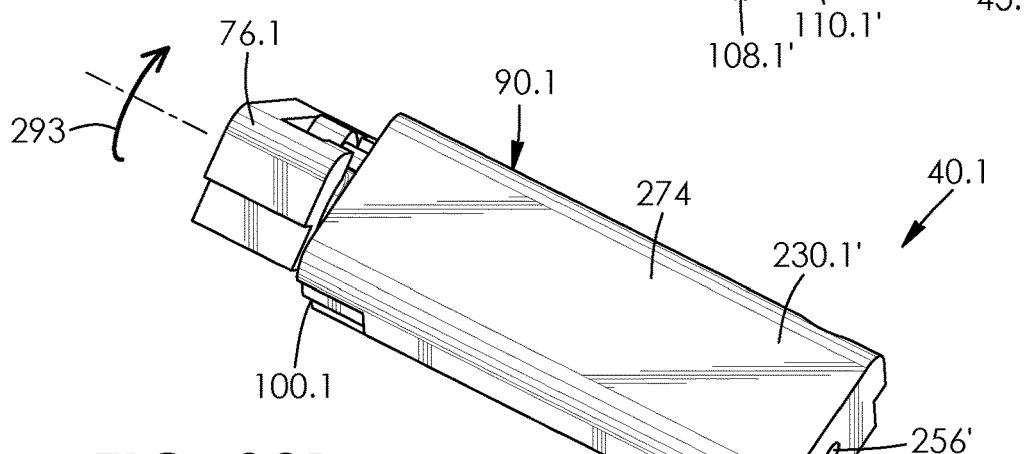
FIG. 32B is a front, top, right side perspective view of the cartridge of FIG. 29, with the retaining member shown in a partially unlocked position.

Referring to FIG. 29, the medicament injector 40.1 includes a retaining member 76.1 which is shaped to retain in place and bias spring 284 towards piston 106.1 and selectively couple to end 100.1 of the cartridge 90.1 as seen in FIG. 32A. In this example and referring to FIG. 29, the cartridge includes a pair of spaced-apart, resilient male members 286 and 288 each of which extend in part about barrel 96.1 and which have enlarged ends 290.

Figure 32C:
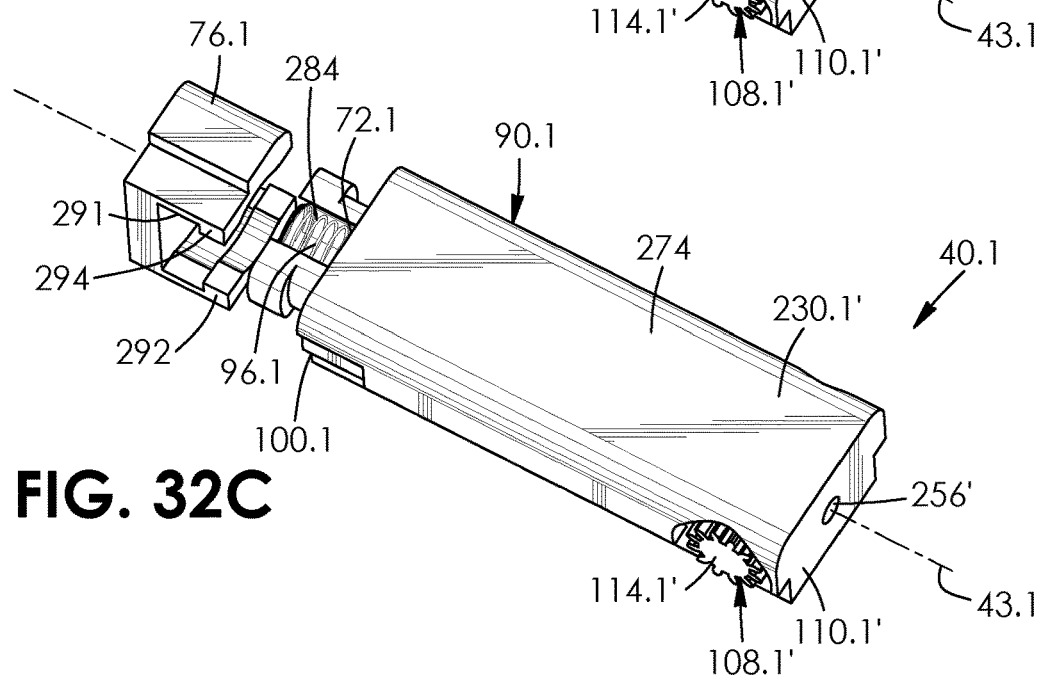
FIG. 32C is a front, top, right side perspective view of the cartridge of FIG. 29, with the retaining member shown in a fully unlocked position and spaced apart from the body of the cartridge.

As seen in FIG. 32C, the retaining member has a complementary shape, in this example in the form of a C-shape with an inner channel 291, and inwardly-extending catches 292 and 294. As seen in FIG. 32C, the retaining member is shaped enclose the male members 286 and 288 in a first angular configuration and insertion position. Rotation of the retaining member thereafter, as shown by arrow 293 in FIG. 32B, causes catches 292 and 294 to fit within corresponding recesses 296 of the male members 286 and 288 in a locked mode. The enlarged ends 290 of the male members are configured to fit within and be enclosed by inner channel 291 of the retaining member 76.1. The retaining member 76.1 holds the spring 284 and barrel 96.1 in place within the cartridge housing 274. Reversing the above steps enable one to selectively access and remove the barrel if desired.

As seen in FIG. 31D, the retaining member 76.1 includes a protrusion, in this example a centrally-positioned knob 298 which extends within channel 291 and which is shaped to fit within open end 278 of barrel 96.1.

As seen in FIG. 31D, the retaining member 76.1 has pair of spaced-apart lower recessed regions 300 and 302 along sides 304 and 306 thereof. As seen in FIG. 35, the retaining member is shaped to slidably extend in part within bore 196 of the cartridge-accepting receptacle 70.1 with protrusions 209 and 211 extending within corresponding the recessed regions 300 of the retaining member.

The above is only one example of one manner of holding barrel 96.1 in place within cartridge housing 90.1 and is not strictly required. Also, in other embodiments, the barrel may be held in place without access thereto being permitted, for example.

In operation and referring to FIG. 33B, in the closed position of the valve 108.1' fluid communication between the cartridge 90.1 and the needle assembly 128 is inhibited. Valve 108.1 further inhibits access to needle 146 when the cartridge is in the pre-injection mode seen in FIG. 33B.

Insertion of the cartridge 90.1 within cartridge-accepting receptacle 70.1, as shown by arrow 308, causes end 110.1 of the cartridge to abut and push against valve housing 230. This causes the valve 108.1 to move towards depressor housing 154. As seen in FIG. 33A, teeth 223 and 225 engage with gears 258 of valve body 114.1, causing the valve 108.1 to move from the closed position seen in FIG. 33B to an open position seen in FIG. 34B. A first barrier to the inner needle 146 is thus removed.

As the cartridge 90.1 continues to be inserted into the cartridge-accepting receptacle 70.1, teeth 223 and 225 engage with gears 258' of valve 108.1' seen in FIG. 34A. This causes valve 108.1' to move from the closed position seen in FIG. 34B to the open position seen in FIG. 35. A second barrier to the medicament 92.1 is thus removed.

As the cartridge 90.1 further continues to be inserted into the cartridge-accepting receptacle, as shown by arrow 310 in FIGS. 34A and 34B, inner needle 146 extends through passageways 116.1 and 116.1' of the valve 108.1 and 108.1' as seen in FIG. 35, and front end 234 of valve housing 230 abuts end 164 of depressor housing 154.

Referring to FIG. 35, medicament is administered to a patient by inserting needle 52.1 into the patient such that flange 134 of depressor 44.1 abuts the patient and biases the depressor inwards, as shown by arrow 312. This causes inner needle 146 to pierce sealed opening 282, extend within barrel 96.1 and access medicament 92.1 as seen in FIG. 37. Thus, inwardly biasing the depressor 44.1 causes the inner needle to be in fluid communication with the cartridge 90.1 so inserted into the cartridge-accepting receptacle 70.1. The spring-biased piston 106.1 thus biases the medicament 92.1 outwards of the barrel when the sealed opening is pierced by the needle as seen by FIG. 37. The medicament is therefore accessible via the inner needle 146.

The medicament is thus accessible via the applicator 42.1 when the cartridge is fully inserted into the cartridge-accepting receptacle. The needle assembly 128 is also therefore selectively in fluid communication with the medicament 92.1 when the cartridge 90.1 is inserted into the applicator 42.1. The cartridge is configured to only enable release of the medicament upon the cartridge being fully inserted into the applicator and the depressor 44.1 being thereafter actuated.

Figure 38:
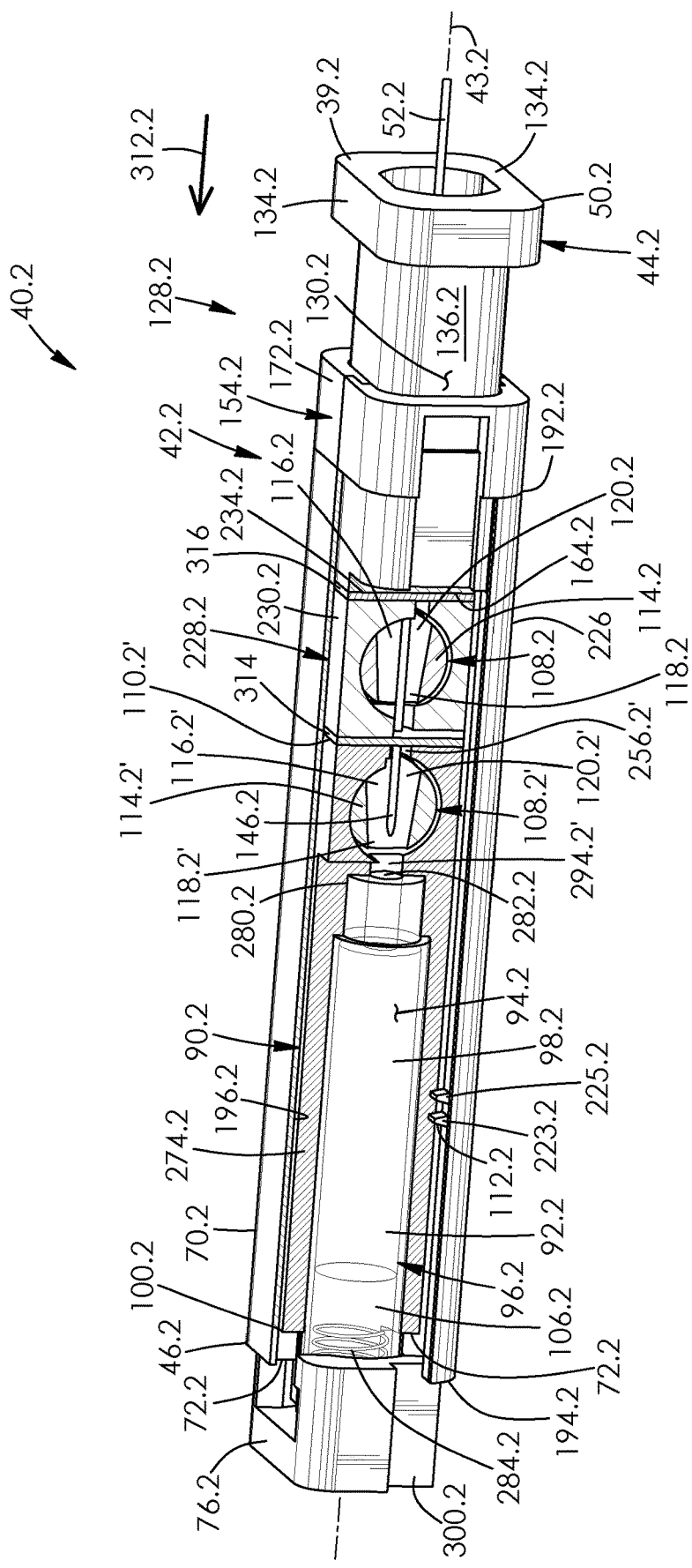
FIG. 38 is a side elevation view of a medicament injector according to a third embodiment.

FIG. 38 shows a medicament injector 40.2 according to a further embodiment. Like parts have like numbers and function as the embodiment shown in FIGS. 20 to 37 with decimal extension "0.2" replacing decimal extension "0.1". Medicament injector 40.2 is substantially the same as medicament injector 40.1 as shown in FIGS. 20 to 37 with the exception that it further includes a pair of seal members, in this example elastoplastic membranes 314 and 316 that are pieced by needle 146.2 when depressor 44.1 is biased inwards as shown by arrow 312.2.

ADDITIONAL DESCRIPTION

Examples of medicament injectors, and interchangeable cartridges therefor, have been described. The following clauses are offered as further description.

(1) A medicament injector comprising: a cartridge applicator including a plunger adjacent to a first end thereof, a conduit shaped to couple with a needle adjacent to a second end of the cartridge applicator, and a cartridge-accepting receptacle between said ends; and an interchangeable cartridge configured to receive or contain a medicament within an interior thereof, the cartridge having a plunger-input end, having a medicament-output end, and including a piston between the ends thereof, whereby insertion of the cartridge into the cartridge-accepting receptacle causes the plunger-input end of the cartridge to be in fluid communication with the plunger, the interior of the cartridge to be in fluid communication with the medicament-output end of the cartridge, and the medicament-output end of the cartridge to be in fluid communication with the conduit of the cartridge applicator.

(2) The medicament injector of clause 1 further including a retaining member slidably coupled to the applicator, the retaining member being biased towards a closed position and, upon being engaged with the cartridge, moving towards an open position in which the cartridge is fully insertable within the cartridge-accepting receptacle, with the retaining member being shaped to inhibit removal of the cartridge thereafter.

(3) The medicament injector of clause 1, wherein the cartridge includes a first one of a catch and a protrusion, and wherein the medicament injector further includes a retaining member slidably coupled to the applicator, the retaining member including a second one of the catch and the protrusion, the retaining member being biased towards position an extended position in which said second one of the catch and the protrusion extends within the cartridge-accepting receptacle, whereby, when the first one of the catch and the protrusion of the cartridge engages with the second one of the catch and the protrusion of the retaining member, the retaining member is moveable from the extended position to a retracted position, in which the cartridge is fully insertable within the cartridge-accepting receptacle of the applicator and the retaining member abuts the cartridge so as to inhibit removal of the cartridge from the cartridge-accepting receptacle.

(4) The medicament injector of any one of clauses 1 to 3 wherein the cartridge includes a hollow body within which the medicament is received and a valve pivotably coupled to said body, the valve being moveable from a closed position in which fluid communication between the hollow body and the medicament-output end of the cartridge is inhibited, to an open position in which fluid communication between the hollow body and the medicament-output end of the cartridge is promoted, the valve being configured to move to said open position upon the cartridge being fully inserted within the cartridge-accepting receptacle.

(5) The medicament injector of any one of clauses 1 to 4, wherein the cartridge includes a valve actuator and wherein the applicator includes a ramp upon which the valve actuator is slidable when the cartridge is being inserted into the cartridge-accepting receptacle, the ramp functioning to move the valve actuator from a closed position in which fluid communication between the medicament and the medicament-output end of the cartridge is inhibited, to an open position in which fluid communication between the medicament and the medicament-output end of the cartridge is promoted.

(6) The medicament injector of any one of clauses 1 to 5 wherein the applicator includes a first one of a male member and a female member, and wherein the cartridge includes a second one of the male member and the female member, the male member being configured to couple with the female member upon the cartridge being fully inserted within the cartridge-accepting receptacle and being configured to inhibit removal of the cartridge from the cartridge-accepting receptacle thereafter.

(7) A medicament injector comprising: a syringe having a cartridge-accepting receptacle; and an interchangeable cartridge including a body shaped to receive or contain a medicament within an interior thereof and including a valve coupled to said body, whereby insertion of the cartridge into the cartridge-accepting receptacle actuates the valve to move from a closed position, in which access to the medicament is inhibited, to an open position in which the medicament is injectable via said syringe.

(8) A medicament injector comprising: a syringe having a cartridge-accepting receptacle; and an interchangeable cartridge including a hollow body shaped to receive or contain a medicament therewithin and including a valve coupled to said body, the valve being configured to only enable release of the medicament upon the cartridge being fully inserted within the syringe.

(9) A kit comprising a plurality of interchangeable cartridges and the medicament injector of any one of clauses 1 to 8.

(10) An interchangeable cartridge shaped to be received within a cartridge-accepting receptacle of a syringe, the cartridge comprising: a hollow body having a bore in which medicament is preloaded, a plunger-input end in communication with said bore, and a valve end; a piston member disposed within the bore and positioned between said ends; and a valve coupled to said valve end of the hollow body, the valve being configured to move from a closed position, in which fluid communication past the valve end is inhibited, to an open position, in which fluid communication past the valve end is promoted, upon being fully inserted into the cartridge-accepting receptacle.

(11) An interchangeable cartridge shaped to be received within a cartridge receptacle of a medicament injector, the cartridge comprising: a body shaped to receive or contain a medicament within an interior thereof; and at least one barrier member having a closed position in which access to the medicament is inhibited, the barrier member moving from the closed position to an open position, in which the medicament is accessible via the applicator, when the cartridge is inserted into the cartridge-accepting receptacle, and the barrier member moving back to the closed position when the cartridge is removed from the cartridge-accepting receptacle.

(12) The cartridge of clause 11, wherein the barrier member is a valve.

The medicament injectors as herein described may provide numerous advantages by for, example, reducing the number of steps and number of components involved in medication delivery via these proposed novel mechanisms to reduce errors and increase speed in time-critical situations to deliver medications. In specific situations, the medicament injector as herein described may make medication delivery easier and safer while reducing the size/bulk of equipment required.

(1) Introduce a novel multi-modular and interchangeable pre-filled medicament cartridge assembly.
(2) The cartridge is pre-filled with medication and designed in such a way to be used with most medications and its associated doses in emergent situations.
(3) The required cartridge selected by the clinical provider for the specific needed clinical situation interfaces/inserts into an accepting injector device that will accommodate the cartridge in a sterile fashion.
(4) Once the cartridge is inserted and loaded into the accepting injector device, pressure applied to the front of the injector device (facing the patient) will further activate a mechanism to deliver the medicament from the cartridge/injector device into the patient.
(5) The user will be able to select the medicament cartridge as needed and load it into the injector device for each given situation/scenario.
(6) This makes the entire process of medication delivery easier, quicker, safer, and saves on the bulk/size of equipment involved.
(7) Sterility is preserved throughout. Mechanism allows for a one direction barrier/sterile seal breaking action to allow medicament penetration into injector device from the loaded cartridge followed by injection into the patient while maintaining closed sterile space of the medication.
(8) Reduction of errors from the reduced cognitive load of simply selecting the needed cartridge and inserting it into the device.
(9) Increased speed of medication delivery means delays in giving life-saving medications can be avoided.
(10) Ease of use for non-trained providers in emergency situations such as first aid delivery of epinephrine in anaphylaxis allergy or naloxone delivery in opioid overdose or antidote to biological/chemical warfare.
(11) Reduced bulk where volume of medications/device is important (aerospace medicine, pre-hospital medicine, military/tactical medicine, and bystander medicine).

It will also be appreciated that many variations are possible within the scope of the invention described herein. It will be understood by someone skilled in the art that many of the details provided above are by way of example only and are not intended to limit the scope of the invention which is to be determined with reference to the following claims.

What is claimed is:

1. A medicament injector comprising:
an applicator including a cartridge-accepting receptacle and a needle; and
an interchangeable cartridge including a body shaped to receive or contain a medicament within an interior thereof and including at least one barrier member rotatable relative to the body, the at least one barrier member having a closed position in which access to the medicament is inhibited, the at least one barrier member having an open position in which the medicament is accessible via the applicator thereby allowing communication between the cartridge and the needle, with the at least one barrier member moving from the closed position to the open position when the cartridge is inserted into the cartridge-accepting receptacle, and the at least one barrier member moving back to the closed position when the cartridge is removed from the cartridge-accepting receptacle.

2. The medicament injector as claimed in claim 1 wherein the applicator includes a first of teeth and a gear and wherein the at least one barrier member includes a second of the teeth and the gear, whereby insertion of the cartridge into the applicator causes the teeth and the gear to engage each other, with the at least one barrier member moving from the closed position to the open position.

3. The medicament injector as claimed in claim 1 wherein the at least one barrier member includes a lever which engages with the applicator when the cartridge is inserted into the applicator and causes the at least one barrier member to move from the closed position to the open position.

4. The medicament injector as claimed in claim 1 wherein the applicator includes a first of a linear gear and a circular gear and wherein the cartridge includes a second of the linear gear and the circular gear, whereby insertion of the cartridge into the applicator causes the gears to engage with each other and causes the at least one barrier member to move from the closed position to the open position.

5. The interchangeable cartridge as claimed in claim 1 shaped to be received within a cartridge-receiving receptacle of a medicament injector.

6. A medicament injector comprising:
an applicator including a cartridge-accepting receptacle; and
an interchangeable cartridge including a body shaped to receive or contain a medicament within an interior thereof and including at least one barrier member rotatable relative to the body, the at least one barrier member having a closed position in which access to the medicament is inhibited, the at least one barrier member having an open position in which the medicament is accessible via the applicator, with the at least one barrier member moving from the closed position to the open position when the cartridge is inserted into the cartridge-accepting receptacle, and the at least one barrier member moving back to the closed position when the cartridge is removed from the cartridge-accepting receptacle.

7. A medicament injector comprising:
an applicator including a body, including a cartridge-accepting receptacle and including at least one barrier member rotatable relative to the body; and
an interchangeable cartridge shaped to receive or contain a medicament within an interior thereof, the at least one barrier member of the applicator having a closed position and being movable from the closed position thereof to an open position thereof, in which the medicament is accessible via the applicator when the cartridge is inserted into the cartridge-accepting receptacle, and the at least one barrier member of the applicator moving back to the closed position when the cartridge is removed from the cartridge-accepting receptacle.

8. The medicament injector as claimed in claim 7 wherein the applicator further includes a depressor, and wherein the cartridge is configured to only enable release of the medicament upon the cartridge being fully inserted into the applicator and the depressor being thereafter actuated.

9. A kit comprising a plurality of interchangeable cartridges and the medicament injector as claimed in claim 7.

10. The medicament injector as claimed in claim 7 wherein the applicator includes a patient-facing portion adapted for variable injection mechanisms including at least one of IM (intramuscular) needle delivery, IV (intravenous) fluid connection delivery with a standard IV tubing and Luer Lock™ mechanism, and IN (intranasal) medicament atomizer delivery.

11. The medicament injector as claimed in claim 7 wherein once the cartridge is inserted into the cartridge-accepting receptacle, delivery of the medicament is determined by at least one of
a plunger mechanism where a partial or complete dose of the medicament is delivered,
a spring-loaded delivery system where an entire volume/dosage of the medicament in a pre-filled said cartridge is delivered, and
a pneumatic delivery system where the entire volume/dosage of the medicament in the pre-filled said cartridge is delivered.

12. A medicament injector as claimed in claim 7, wherein the cartridge includes a body and wherein the cartridge includes at least one barrier member rotatable relative to the body thereof, the barrier member of the cartridge having a closed position in which access to the medicament is inhibited, with the barrier member of the cartridge moving from the closed position to an open position, in which the medicament is accessible, when the cartridge is inserted into the cartridge-accepting receptacle.

13. The medicament injector as claimed in claim 12, wherein the barrier member of the cartridge has a first position in which access to the medicament is inhibited, and wherein the barrier member of the cartridge is moveable in a first direction of rotation from the first position to a second position, in which the medicament is accessible via a needle when the cartridge is inserted into the cartridge-accepting receptacle, with further rotation of the barrier member of the cartridge past said second position in said first direction of rotation being inhibited.

14. The medicament injector as claimed in claim 12, wherein the applicator is connectable to a needle via which the medicament is accessible when the barrier members are in said open positions, wherein the barrier member of the cartridge has a first position in which fluid communication between the needle and the medicament is inhibited, and wherein the barrier member of the cartridge is rotatable to move from the first position thereof to a second position in which fluid communication between the needle and the medicament is enabled.

15. The medicament injector as claimed in claim 12, wherein the barrier member of the cartridge is configured to move back to the closed position thereof when the cartridge is removed from the cartridge-accepting receptacle.

16. The medicament injector as claimed in claim 7, wherein the at least one barrier member is a valve coupled to the body.

17. The medicament injector as claimed in claim 16 wherein the valve is received within and rotatable relative to the body from the closed position to the open position.

18. The medicament injector as claimed in claim 7, wherein the applicator includes a needle assembly that is selectively in fluid communication with the medicament when the cartridge is inserted into the applicator, the needle assembly coupling to and being resiliently biased outwards from the cartridge-accepting receptacle.

19. The medicament injector as claimed in claim 18 further including a second barrier member interposed between the needle assembly and the cartridge, the second barrier member having a closed position in which fluid communication between the cartridge and the needle assembly is inhibited, and the second barrier member being movable from the closed position thereof to an open position thereof, in which the medicament is accessible via the applicator when the cartridge is inserted into the cartridge-accepting receptacle.

20. The medicament injector as claimed in claim 7, wherein the cartridge has a pre-injection mode in which access to the medicament is inhibited, and insertion of the cartridge into the cartridge-accepting receptacle causes the cartridge to move from the pre-injection mode to an injection mode in which the medicament is accessible via a needle.

21. The medicament injector as claimed in claim 20 including a first said barrier member which inhibits access to the medicament when the cartridge is in the pre-injection mode and a second said barrier member which inhibits access to the needle when the cartridge is in the pre-injection mode.

22. The medicament injector as claimed in claim 7, including a reversible barrier mechanism comprising the at least one barrier member.

23. The medicament injector as claimed in claim 7, wherein the applicator is connectable to a needle via which the medicament is accessible when the at least one barrier member is in the open position.

24. The medicament injector as claimed in claim 23 wherein the needle is selectively in fluid communication with the medicament when the cartridge is inserted into the applicator.

25. The medicament injector as claimed in claim 2 further including a second barrier member interposed between the needle and the cartridge, the second barrier member having a closed position in which fluid communication between the cartridge and the needle is inhibited, and the second barrier member being movable from the closed position thereof to an open position thereof, in which the medicament is accessible via the applicator when the cartridge is inserted into the cartridge-accepting receptacle.

26. The medicament injector as claimed in claim 23 wherein the applicator includes a depressor actuation of which causes the medicament to be in fluid communication with the needle.

27. The medicament injector as claimed in claim 23 further including a depressor to which the needle is coupled and outwardly extends, the depressor being resilient biased outwards relative to the cartridge-accepting receptacle, whereby inwardly biasing the depressor causes the needle to be in fluid communication with the cartridge so inserted into the cartridge-accepting receptacle.

28. The medicament injector as claimed in claim 23 wherein the cartridge includes a barrel with a sealed opening and a piston, and wherein a resilient member is configured to bias the medicament outwards of the barrel when the sealed opening is pierced by the needle.

29. The medicament injector as claimed in claim 7, wherein the barrier member is positioned within the body of the applicator.

30. An interchangeable cartridge for a medicament injector, the medicament injector connectable to a needle and including an applicator with a cartridge-accepting receptacle, the interchangeable cartridge comprising:
    a body shaped to receive or contain a medicament within an interior thereof; and
    at least one barrier member rotatable relative to the body, the at least one barrier member having a closed position in which access to the medicament is inhibited, the at least one barrier member having an open position in which the medicament is accessible via the applicator thereby allowing communication between the cartridge and the needle, with the at least one barrier member moving from the closed position to the open position when the cartridge is inserted into the cartridge-accepting receptacle, and the at least one barrier member moving back to the closed position when the cartridge is removed from the cartridge-accepting receptacle.

\* \* \* \* \*